United States Patent
Dougherty et al.

(10) Patent No.: US 10,321,919 B2
(45) Date of Patent: Jun. 18, 2019

(54) POWERED ENDOSCOPE DRILLING DEVICE

(71) Applicant: Tenjin LLC, Brazoria, TX (US)

(72) Inventors: Christopher P. Dougherty, Rogers, AR (US); Gary R. Heisler, Brazoria, TX (US); Robert A. Van Wyk, St. Pete Beach, FL (US)

(73) Assignee: TENJIN LLC, Brazoria, TX (US)

(*) Notice: Subject to any disclaimer, the term of this patent is extended or adjusted under 35 U.S.C. 154(b) by 425 days.

(21) Appl. No.: 15/288,509

(22) Filed: Oct. 7, 2016

(65) Prior Publication Data

US 2017/0100136 A1   Apr. 13, 2017

Related U.S. Application Data

(60) Provisional application No. 62/284,714, filed on Oct. 7, 2015.

(51) Int. Cl.
| | |
|---|---|
| *A61B 17/16* | (2006.01) |
| *A61B 17/32* | (2006.01) |
| *A61B 17/00* | (2006.01) |

(52) U.S. Cl.
CPC ..... *A61B 17/1617* (2013.01); *A61B 17/32002* (2013.01); *A61B 2017/00477* (2013.01); *A61B 2017/320012* (2013.01)

(58) Field of Classification Search
CPC .............. A61B 17/1617; A61B 17/32002
See application file for complete search history.

(56) References Cited

U.S. PATENT DOCUMENTS

| | | | |
|---|---|---|---|
| 8,961,519 B2* | 2/2015 | Gillard | A61B 17/1633 606/80 |
| 2007/0215190 A1* | 9/2007 | Efinger | B08B 9/00 134/166 R |
| 2009/0177202 A1* | 7/2009 | May | A61B 17/32002 606/79 |
| 2012/0203230 A1* | 8/2012 | Adams | A61B 17/32002 606/80 |
| 2016/0287264 A1* | 10/2016 | Chegini | A61B 17/1617 |
| 2017/0354431 A1* | 12/2017 | Rubin | A61B 17/32002 |

* cited by examiner

*Primary Examiner* — Andrew Yang
(74) *Attorney, Agent, or Firm* — Chalin A. Smith; Smith Patent, LLC

(57) ABSTRACT

Described herein are specialized endoscopic drilling devices that may be readily powered by a conventional shaver handpiece and further may be utilized to secure a soft tissue graft to a boney surface. More particularly, the devices, systems and methods of the present invention enable the efficient and minimally invasive formation of off-axis sockets and/or tunnels in boney surfaces that may then serve as a site for graft placement by aperture and/or suspensory fixation means. As such, the present invention has particular applicability to the surgical repair and reconstruction of torn or ruptured tissues, such as ligaments and tendons, in the leg, knee and shoulder, for example.

10 Claims, 18 Drawing Sheets

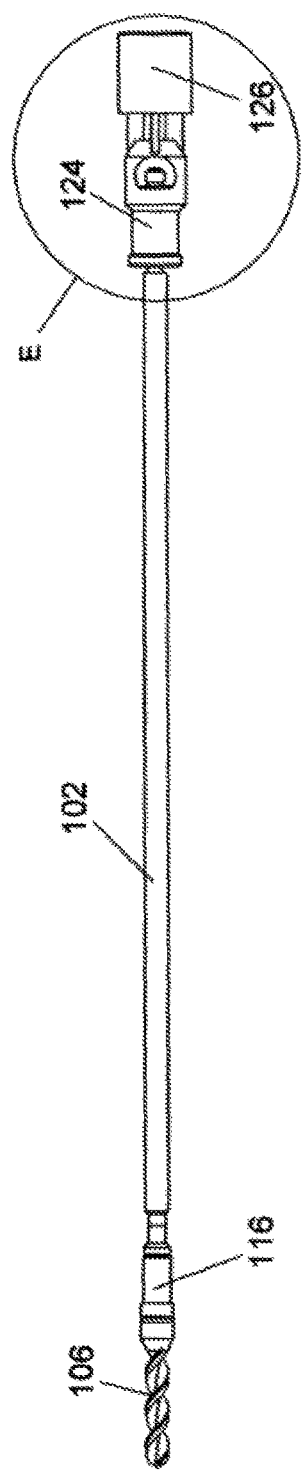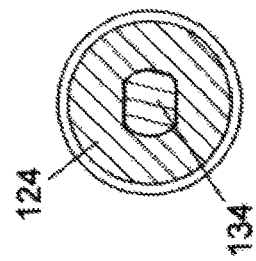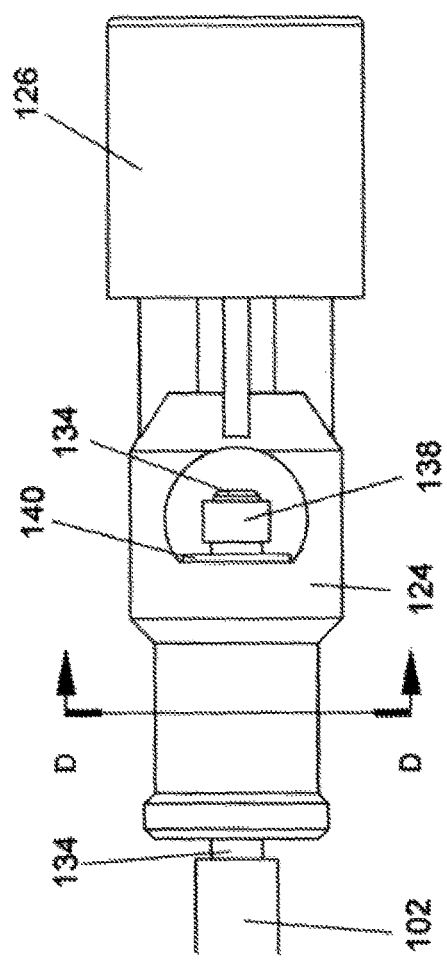
Fig. 4
Fig. 6
Fig. 5

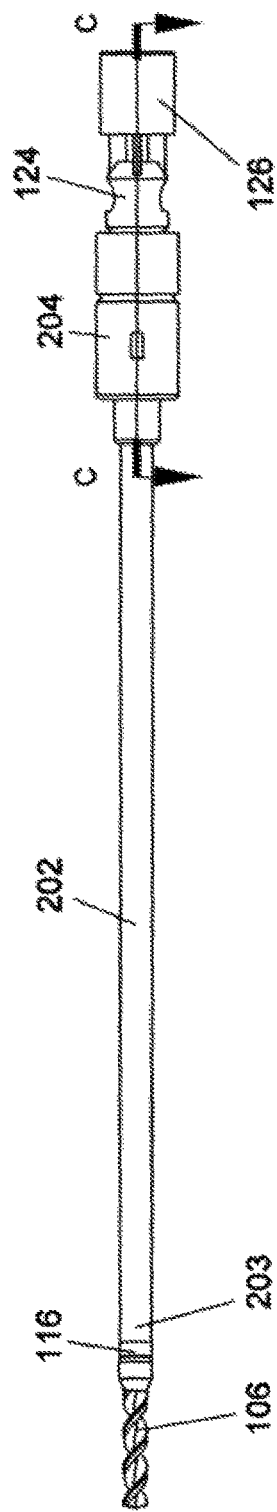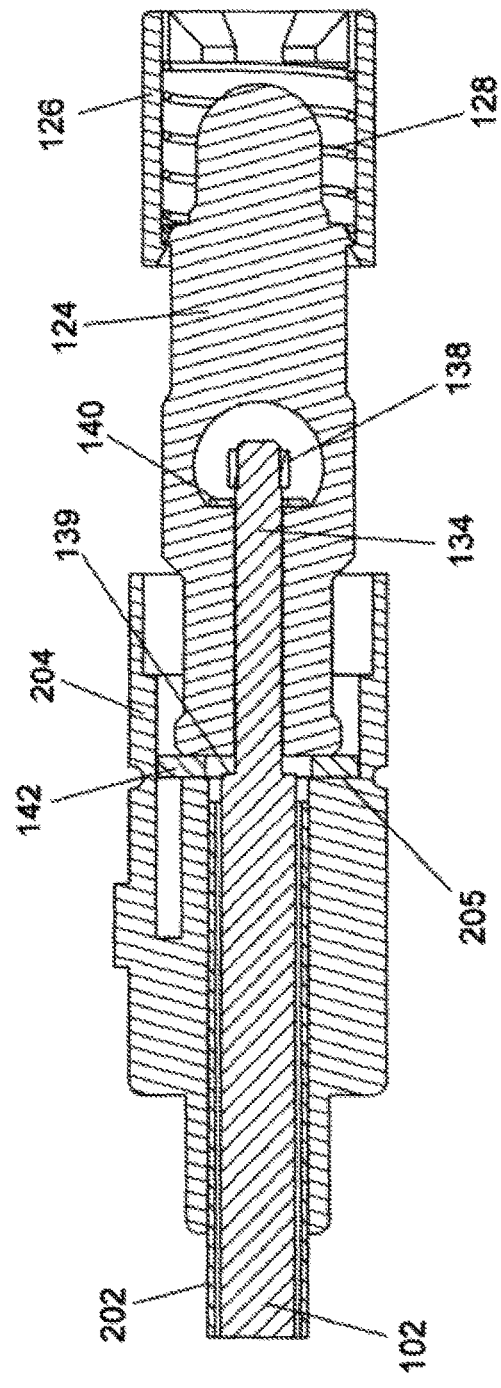
Fig. 14
Fig. 15

POWERED ENDOSCOPE DRILLING DEVICE

PRIORITY

This application claims the benefit of U.S. Provisional application Ser. No. 62/284,714 filed Oct. 7, 2015, the contents of which are hereby incorporated by reference in their entirety.

TECHNICAL FIELD OF THE INVENTION

The present invention relates generally to the field of endoscopic and arthroscopic surgery, more particularly, to methods and systems for securing a soft tissue graft to a boney surface and/or hard tissue by means of a surgically introduced hole, tunnel or "socket". The present invention has particular applicability to those surgical procedures that require the production of off-axis sockets.

BACKGROUND OF THE INVENTION

The use of implants to affix tissue grafts to bone is well known in the orthopedic arts. Common procedures in which such implants are used include, for example, the repair of rotator cuff tears, the repair of torn ligaments in the knee, among others. In these procedures, a socket is drilled or punched in the bone at the attachment site and a graft is secured to the bone using an implant placed in the socket. The graft may be secured to the implant by sutures, or, alternatively, an end of the graft may be placed in the socket and secured directly by an implant. Various devices, systems, and methods for attaching soft tissue grafts, such as ligaments and tendons, to boney surfaces are described in detail in U.S. Pat. No. 9,226,817 and U.S. Pub. No. 2016/0157,852 A1, both to Dougherty et al., as well as the following co-pending Continuation-in-Part applications that claim priority thereto: U.S. Ser. Nos. 15/256,815, 15/256,838, and 15/256,945, all filed Sep. 6, 2016. The contents of these prior disclosures are hereby incorporated by reference herein in their entirety.

In certain procedures, the implant-receiving socket must be formed in the bone by drilling rather than punching. In these cases, a twist drill bit is conventionally mounted in to a powered surgical drilling device. Examples of such configurations are commercially available under tradenames such as the Arthrex 600 Large Bone Power System or the Arthrex 300 Small Bone Power System by Arthrex, Inc. (Naples, Fla.). In addition, Conmed Corporation (Utica, N.Y.) offers a drill chuck that may be removably mounted in an endoscopic shaver handpiece. Such a device, known in commercial circles as a "Thorne Chuck", is a reusable device into which conventional twist drills may be mounted. In all of these conventional drilling systems, the devices are reusable, thereby necessitating cleaning and sterilization between uses, a requirement that has significant impact on cost and constrains scheduling. Additionally, the use of these reusable devices presents opportunities for infection if/when the devices are not cleaned and sterilized properly.

A further limitation of commercially available drilling devices and systems relates to the sockets produced. To that end, many of the drilling devices and systems of the prior art are generally only able to produce sockets that are coaxial with the driving device axis of rotation. Accordingly, specialized systems have been developed that allow the formation of off-axis holes in boney surfaces through the use of a drill driven by a flexible member that transmits torque from the driving handpiece. Illustrative examples of such "off-axis" devices include, for example, the Pivot Phoenix system by Stryker, Inc. (Kalamazoo, Mich.), which is used for drilling small diameter holes in microfracture procedures. The location and angle of entry of the drill into the bone is determined by a separate guide through which the drill is introduced. Unfortunately, using such devices is difficult for the surgeon since he must hold both the guide and the drill while a third hand is required to hold the endoscope. In many cases, the guide distal end will shift during use resulting in misplacement and/or misalignment of the resulting drilled hole. Indeed, when standard drilling devices are used to produce an off-axis hole, the drill must have a flexible torque-transmitting drive portion. Furthermore, a separate guiding device is required to direct the distal drilling portion to the desired location at the desired angular orientation. The use of these guiding devices is problematic for the surgeon as it requires controlling both the powered drilling device and the guiding device.

In the above-cited U.S. Pat. No. 9,226,817 to Dougherty et al., a disclosure that is incorporated by reference herein in its entirety, implant systems and methods are described that allow an implant to be placed in a location(s) that cannot be reached by conventional procedures, e.g., using a rigid linear placement system. The anchor placement systems described by Dougherty et al. include a distal portion that may be angularly offset from the proximal, torque-producing portion(s) of the system. As discussed in detail therein, there is a significant need in the art for drilling systems that can produce the required "off axis" sockets. Such "off axis" sockets may also be utilized for the placement of suture-based "soft" anchors that need not be threaded into the socket, but rather may be easily inserted into the socket and then deployed by applying tension to sutures attached to the anchor. Illustrative examples of such anchoring systems include, but are not limited to, the Draw Tight Suture Anchors by Parcus Medical, Inc. (Sarasota, Fla.), and the Y-Knot RC All-Suture Anchor System by Conmed Corporation (Utica, N.Y.).

Co-pending U.S. patent application Ser. No. 15/142,120 filed Apr. 29, 2016, also to Dougherty et al. and also incorporated by reference herein, describes an improved method for ACL and PCL repair and reconstruction by means of interference screw fixation using implant placement systems that have a distal portion that is angularly offset from the torque-producing proximal portion. The '120 disclosure further describes forming the requisite tunnels for the grafts using a drilling device that is powered by an arthroscopic shaver handpiece and that includes a distal portion angularly offset from the proximal torque-producing portion of the device.

While the Dougherty systems and methods constitute significant advances in the fields of endoscopic and arthroscopic surgery, particularly in the area of ligament and tendon repair, there nevertheless remains a clear need for additional shaver handpiece-powered disposable endoscopic drilling devices. For example, while an endoscopic drilling device of a rigid linear construction would have significant utility, a device having a fixed angular offset between the distal drilling portions of the device and the more proximal portions would allow surgeons to form tunnels and sockets in locations in which an equivalent rigid linear device could not. Still more desirable is a drilling device in which the distal portion may be angularly offset by the surgeon at the time of use, wherein the angular offset may be optimized by the surgeon to suit the procedure to be performed.

Numerous other surgical procedures also involve the drilling of holes in boney surfaces and solid tissues. For example, microfracture is commonly used to treat damaged articular cartilage. The procedure generally involves drilling or punching a pattern of holes into a properly prepared boney surface. Current techniques use a microfracture awl that is driven into the bone using a mallet, or, alternatively, use specialized drilling devices such as the PowerPicks by Arthrex, Incorporated (Naples, Fla.). However, such techniques have significant drawbacks, primarily stemming from difficulties in accessing certain locations and in consistently producing holes with the desired geometry. With regard to the latter, access to locations that are not in line with the axis of the awl is frequently required. In such cases, it becomes necessary to drive into the surface an awl having an off-axis pointed distal tip. Such techniques are rife with problems, including the inefficient application of the mallet, which poses the risk of injury to the surgeon's hands and frequently results in "skiving", a condition in which the awl's pointed distal end does not cleanly penetrate the surface but rather skids along the surface, producing a groove. In addition, many of the conventional off-axis devices, such as the PowerPick device, have an off-axis distal treatment portion formed at a fixed angle to the axis. This fixed arrangement is frequently problematic, particularly when the maximum formed angle of the devices is insufficient or not suitable for allowing the drilling of a hole having an axis substantially normal to the boney surface, a condition that greatly enhances the likelihood of successful treatment.

In view of the aforementioned problems and deficiencies present in the arthroscopic and endoscopic arts, there remains a need for a microfracture drill that may be powered by a shaver handpiece and that, in operation, does not require the use of a separate guiding device to produce off-axis holes. There is further a need in the art for such a device to include a distal portion that may be bent and rebent by the surgeon to an optimum offset so as to produce an array of holes having axes substantially normal to the boney surface. The present invention addresses both of these needs.

SUMMARY OF THE INVENTION

Shavers are used in virtually all arthroscopy procedures. Accordingly, a powered shaver handpiece is considered standard equipment in most operating rooms and is thus readily available to virtually every orthopedic surgeon. In addition, arthroscopic shavers and burrs provided with a distal portion angularly offset from the axis of the shaver handpiece and device proximal portion are well known in the art. Generally, the distal portions of such devices are fixedly formed to the desired angular offset during manufacture, with typical offsets being twenty degrees or less. Specialized bending fixtures and dies are used to produce repeatable bends with small radii. Other powered arthroscopic devices, such as the Merlin line of shaver blades produced by Conmed (Utica, N.Y.), are supplied to the surgeon without an angular offset but allow the surgeon to bend the device to the desired offset in the operating room. In these latter case, a bending device is supplied; such devices generally producea large bend radius distributed along the length of the distally extending outer tube. Accordingly, while presently available arthroscopic shavers and burrs may be supplied either as a pre-bent configuration or are bendable in the field, none are both pre-bent and bendable in the field.

The elongate outer tubular elements used for the distal portions of arthroscopic shavers and burrs have uniform structural properties throughout their length. Bending of these outer tubular elements during manufacture allows the use of dies and other tooling which are able to repeatably produce bends having a small radius. Attempting to modify the angular offset of such a pre-bent device results not in modification of the original bend, but in bending at locations on the tubular member adjacent to the bend produced during manufacture. Forming the original bend in the outer tubular element during manufacture work-hardens the material in the bent region; as such, any attempt to modify the bend will cause adjacent regions that have not been work-hardened to deform. For this reason, bendable-in-the-field products like the Conmed Merlin shaver blade are typically provided with large radii such that significant work-hardening of the tubing does not occur. While these bendable devices can be bent to an initial angular offset and then re-bent to another offset, the large bend radii severely limit the utility of the bendable devices.

The present invention incorporates a distal tubular element having a non-uniform flexural strength throughout its length. Specifically, in the context of the present invention, the flexural strength of a portion of the tube near the device distal end is reduced such that the surgeon can impart an initial angular offset to the distal portion in the operating room to suit the requirements for a specific procedure and location using of a manual bending device. The angular offset of the tube distal end may then be readily and repeatedly adjusted and readjusted by modifying the degree of angular offset, with the deformation of the tube remaining localized in the bend region since adjacent portions of the tube have a higher flexural strength. As discussed in detail in U.S. Publication No. 2015/0245868 and its continuation-in-part, co-pending U.S. application Ser. No. 15/252,873 filed Aug. 31, 2016, both to Dougherty et al. and both incorporated by reference herein, the flexural strength in the bend region may be reduced by any number of different mechanisms, for example, by notching the tube in the bend region, by annealing the tube in the bend region, by reducing the wall thickness in the bend region, or by utilizing a material having lower flexural and/or yield strength to form the bend region, or, alternatively, by any combination of these means. All are considered to fall within the purview of the present invention.

Arthroscopy burrs, whether straight or pre-bent, are generally provided with distal bearings that prevent deflection when the rotating cutting portion is subjected to lateral loading. The resistance to proximal axial loading is supplied solely by a spring that maintains the distal axial position of the inner assembly relative to the outer assembly. As such, this standard construction is not suited to axial loading, as occurs when drilling, since the inner rotating assembly will simply deflect proximally compressing the spring. Critically, there is no bearing present which resists proximal axial loading.

In an attempt to address certain limitations of prior art devices, Trott in U.S. Pat. No. 5,851,208 describes a pre-bent surgical burr having a distal bearing that resists proximal axial forces in which the cutting element is rotatably affixed to the distal end of a tubular outer member. A rotatable inner member selectively engages with the proximal end of the cutting element so that the inner assembly may be disassembled from the outer assembly for removing clogs in the device's aspiration path. The inner member also includes a plurality of drive links that adds complexity to the device. However, in contrast to the present invention, the Trott device may not be fairly characterized as "rebendable" since the bend imparted to the outer tubular member at manufacture work hardens the material thereby preventing modification of the offset angle.

Accordingly, it is an objective of the present invention to construct an endoscopic drilling device that may be single-use and that may be powered by a conventional arthroscopy shaver handpiece. The construction of the device of the present invention is similar to that of a conventional shaver or burr in that the inventive device has a non-rotating outer tubular member and an inner rotating member that transmits torque to the distally mounted drill or other cutting device. However, the device of the present invention is further provided with a distal bearing that maintains the axial position of the inner assembly when the device is subjected to the axial forces required for drilling. In a first preferred embodiment, the device may be rigidly linear and have a distal drilling member that is coaxial with the axis of the driving device. In an alternatively preferred embodiment, the outer tubular member may be provided with a distal portion that is angularly offset from the more proximal portions of the tubular member and outer hub. In this latter embodiment, at least a portion of the inner driving member is flexible so that it may transmit torque to the distally mounted, angularly offset drilling element.

In other embodiments of the present invention, the angular offset between the distal and proximal portions of the device may be formed by the manufacturer and cannot be modified by the surgeon. Such devices may be produced in a range of angular offsets so that the surgeon may select the device that has the most suitable offset for the procedure to be performed. However, in other more preferred embodiments, the angular offset between the distal portion and the proximal portion may be modified by the surgeon; in this manner, the location and orientation of a socket, tunnel or hole for graft attachment may be optimized. The devices of the present invention may be provided to the surgeon as linear devices, or, alternatively, with the distal portion having an initial angular offset. In either case, the angular offset of the distal portion may be optimized by the surgeon in the operating room, using a bending device configured for that purpose.

Typically, when shavers, burrs and other device attachment are removably mounted in a powered shaver handpiece, an inner hub engages a shaft in the handpiece so as to transmit torque, and the outer hub is confined within a distal cylindrical recess of the handpiece. Because clearance must exist between the outer hub and this distal recess, the device placed therein is not rigidly mounted to the handpiece, but rather can be angularly deflected relative to the handpiece due to the clearance between the outer hub and the distal recess. While this angular deflection has only a minimal effect when using shavers or burrs, the deflection may have a greater effect in the context of an endoscopic drilling device in accordance with the present invention mounted in a shaver handpiece as rigidly locating the distal end of the drilling element during initiation of hole drilling is essential. In the absence of this requisite rigidity, the drill may "walk" away from the intended hole location, thereby resulting in the misplacement of the socket or tunnel.

Thus, it is an objective of the present invention to address this issue by, in certain embodiments, minimizing the deflection of the device mounted in the handpiece and increasing the rigidity of the juncture between the mounted device and the endoscopic shaver handpiece through the use of a novel stabilizing device. In the context of the present invention, the stabilizing device may take the form of a large wingnut including a first threaded portion that engages with a second threaded portion added to the distal end of the outer hub of the device inserted in the shaver handpiece. In certain embodiments, stabilizer/wingnut may be tightened against the distal end of the handpiece. In yet other embodiments, the stabilizer may have a diameter of sufficient size that engagement with the handpiece distal end provides a resistance to angular deflection of the device.

These and other aspects are accomplished in the invention herein described. Further objects and features of the invention will become more fully apparent when the following detailed description is read in conjunction with the accompanying figures and examples. However, it is to be understood that both the foregoing summary of the invention and the following detailed description are of a preferred embodiment, and not restrictive of the invention or other alternate embodiments of the invention. For example, while use of powered endoscopic drilling devices of the present invention is described herein with regard to forming sockets for implant placement and for producing an array of small diameter holes for microfracture treatment of articular cartilage lesions, those of skill in the art will readily appreciated that such devices may be used in virtually any procedure in which the drilling of a hole is required, particularly a hole in a remote and/or difficult to access, often off-axis location. For instance, a transosseous tunnel (a tunnel through a bone) is used in many procedures. Devices of the present invention may be used to create transosseous tunnels that are coaxial with the axis of the handpiece, or angularly offset from the axis. Other drilling operations, such as drilling suture holes in the bone plugs of bone-tendon-bone grafts for ACL or PCL repair may also be performed with devices of the present invention. Accordingly, the foregoing and following description is merely illustrative of the present invention and should not constructed as limiting of the construct, design and utility of the present invention.

BRIEF DESCRIPTION OF THE FIGURES

Various aspects and applications of the present invention will become apparent to the skilled artisan upon consideration of the brief description of figures and the detailed description of the present invention and its preferred embodiments that follows:

FIG. 4 is a plan view of the objects of FIG. 1.

FIG. 5 is an expanded view of the objects of FIG. 4 at location E.

FIG. 6 is a sectional view of the objects of FIG. 5 at location D-D.

FIG. 14 is a side elevational view of the objects of FIG. 12.

FIG. 15 is a sectional view of the proximal portion of the objects of FIG. 14 at location C-C.

DETAILED DESCRIPTION OF THE PREFERRED EMBODIMENTS

Figure 1:
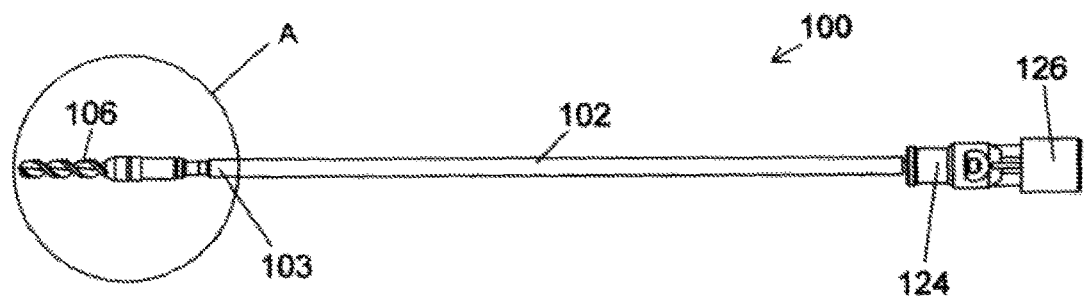
FIG. 1 is a plan view of an inner drive assembly for an endoscopic drilling device of the present invention.
Figure 2:
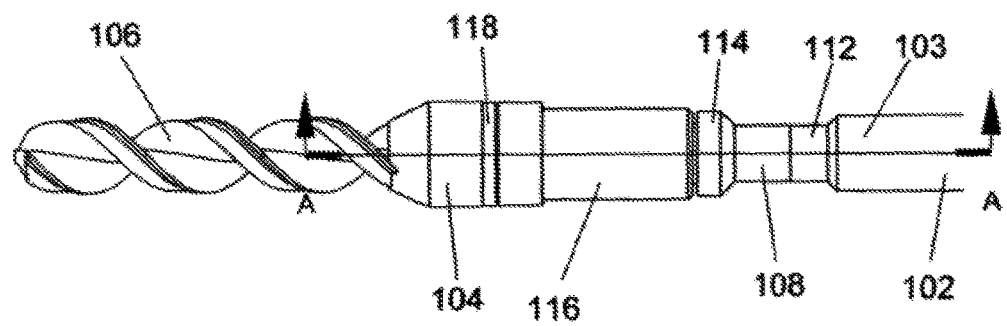
FIG. 2 is an expanded view of the distal portion of the objects of FIG. 1 at location A.
Figure 3:
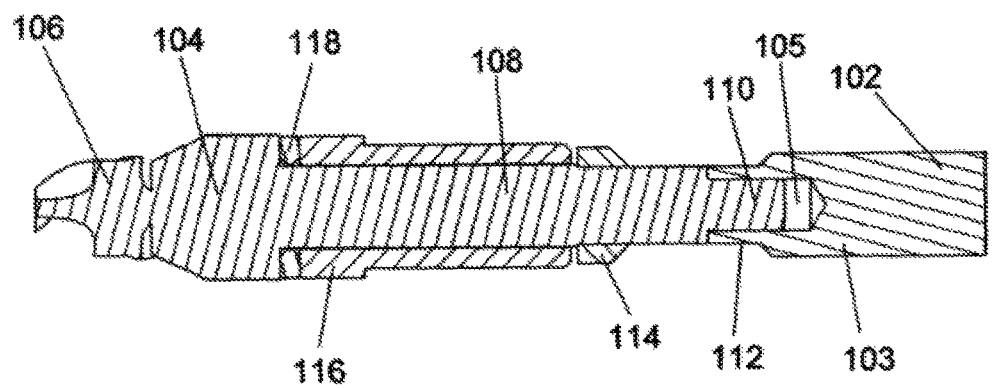
FIG. 3 is a sectional view of the objects of FIG. 2 at location A-A.
Figure 7:
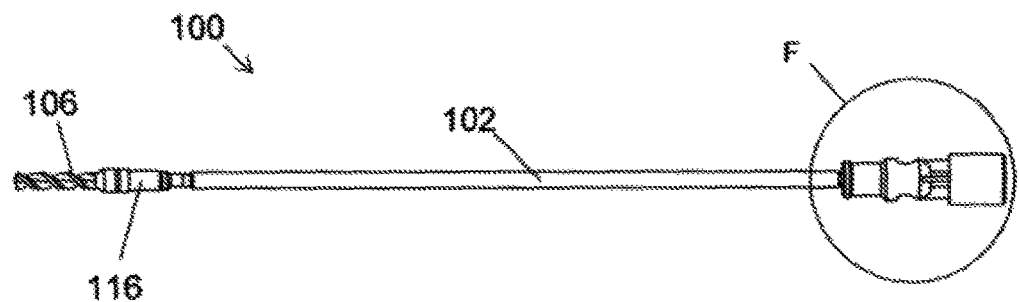
FIG. 7 is a side elevational view of the objects of FIG. 1.
Figure 8:
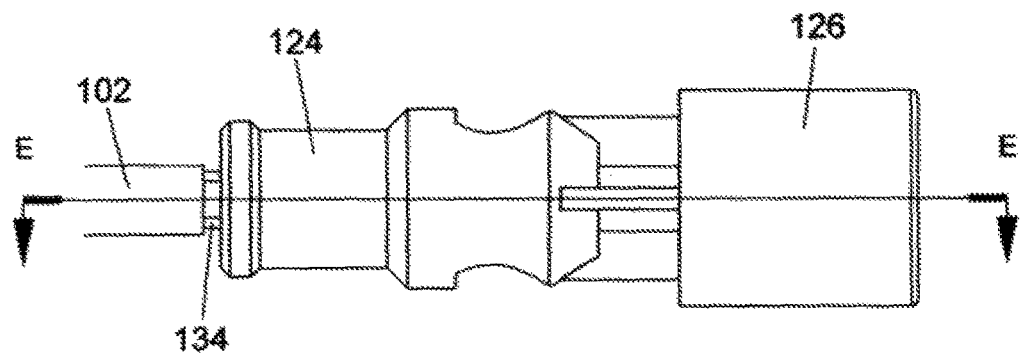
FIG. 8 is an expanded view of the proximal portion of the objects of FIG. 7 at location F
Figure 9:
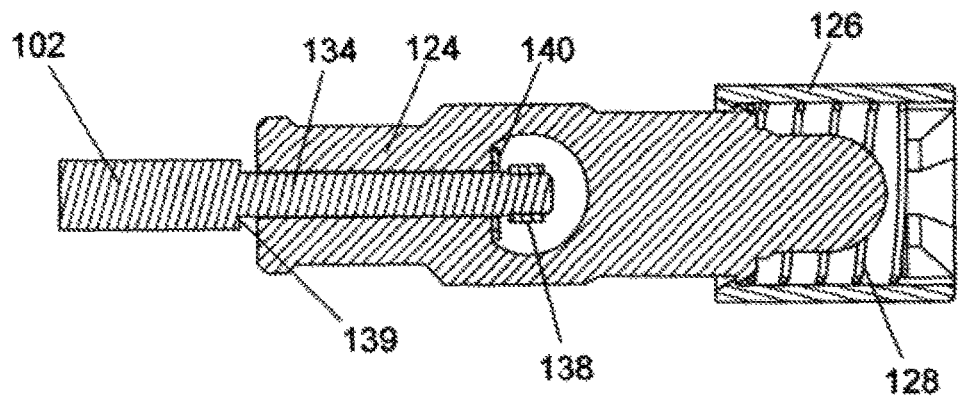
FIG. 9 is a sectional view of the objects of FIG. 8 at location E-E.

Although any methods and materials similar or equivalent to those described herein can be used in the practice or testing of embodiments of the present invention, the preferred methods, devices, and materials are now described. However, before the present materials and methods are described, it is to be understood that the present invention is not limited to the particular sizes, shapes, dimensions, materials, methodologies, protocols, etc. described herein, as these may vary in accordance with routine experimentation and optimization. It is also to be understood that the terminology used in the description is for the purpose of describing the particular versions or embodiments only, and is not intended to limit the scope of the present invention which will be limited only by the appended claims. Accordingly, unless otherwise defined, all technical and scientific terms used herein have the same meaning as commonly understood by one of ordinary skill in the art to which the present invention belongs. However, in case of conflict, the present specification, including definitions below, will control.

In the context of the present invention, the following definitions apply:

The words "a", "an" and "the" as used herein mean "at least one" unless otherwise specifically indicated. Thus, for example, reference to an "opening" is a reference to one or more openings and equivalents thereof known to those skilled in the art, and so forth.

The term "proximal" as used herein refers to that end or portion which is situated closest to the user of the device, farthest away from the target surgical site. In the context of the present invention, the proximal end of an arthroscopic device of the present invention includes the driver and handle portions.

The term "distal" as used herein refers to that end or portion situated farthest away from the user of the device, closest to the target surgical site. In the context of the present invention, the distal end of an arthroscopic repair system of the present invention includes one or more components adapted to address the patient's body, for example, a distal drilling element.

In the context of the present invention, the term "cannula" is used to generically refer to the family of rigid or flexible, typically elongate lumened surgical instruments that facilitate access across tissue to an internally located surgery site.

In the context of the present invention, the term "cannulated" is used to generically refer to the family of rigid or flexible, typically elongate surgical instruments having a central lumen into which an elongate device such as a guide wire or guide pin may pass so as to prevent the cannulated device from deviating from a selected path during use.

The terms "tube" and "tubular" are interchangeably used herein to refer to a generally round, long, hollow component having at least one central opening often referred to as a "lumen".

The terms "lengthwise" and "axial" are used interchangeably herein to refer to the direction relating to or parallel with the longitudinal axis of a device. The term "transverse" as used herein refers to the direction lying or extending across or perpendicular to the longitudinal axis of a device.

The term "lateral" pertains to the side and, as used herein, refers to motion, movement, or materials that are situated at, proceeding from, or directed to a side of a device or patient.

The term "medial" pertains to the middle, and as used herein, refers to motion, movement or materials that are situated in the middle, in particular situated near the median plane or the midline of the device or subset component thereof or of a patient.

The present invention contemplates repeatedly flexing, bending or angling the distal region of an endoscopic device to a wide range of angles relative to the longitudinal axis of the device, such angles ranging from greater than 0 to about 90 degrees, preferably from about 5 to about 60 degrees, more preferably from about 10 to about 45 degrees, even more preferably from about 10-20 to about 30-40 degrees.

To facilitate bending, the present invention contemplates providing the elongate distal tubular member of an endoscopic device with a non-uniform flexural strength throughout its length. In the context of the present invention, the term "flexural strength", also known as yield strength or bend strength, is a mechanical parameter of a material or component defined as its ability to resist inelastic transverse deformation under load that can be readily quantified and compared using conventional assays, such as the transverse bending test.

In the Examples below, the present invention makes reference to "notches" on opposing sides of a distal tubular member. In the context of the present invention, the term "notch" refers to a preferably long, narrow indentation, aperture, or incision disposed at an edge or surface. Although the notches described hereinbelow are depicted as generally "V-shaped" or "cylindrical" or "circular", it will be readily apparent to the skilled artisan that the shape may be readily varied; for example, the notches may have a non-uniform and/or non-linear (i.e., curved) profile.

In the Examples below, respective sets of notches or apertures are preferably offset such that the notches on one side are centered between notches on the opposite side. It is these notches that serve to reduce the flexural strength of the device and thus permit bending in the distal region. However, as noted above, alternate mechanisms for reducing flexural strength are contemplated including, for example, reducing the wall thickness in the bend region, annealing the tube in the bend region, or by utilizing a material having lower flexular and/or yield strength to form the bend region.

The term "convex" is used herein to describe an element (s) that has a shape like the outside of a bowl, that is curved or rounded outward like the exterior of a sphere of circle. Alternatively, the term "concave" is used herein to describe an element that has a shape like the inside of a bowl, hollowed, curving or rounded inward like the inside of a sphere or circle. In the context of the present invention, when the device is flexed in a "downward" direction (relative to the longitudinal axis of the device), the "top" side that makes up the "outside" of the curve is referred to herein as the "convex side", whereas the "bottom" side that makes up the "inside" of the bend is referred to as the "concave side". The components are reversed when the device is flexed in an "upward" direction relative to the longitudinal axis of the device. In that case, the top side is the concave side and the bottom side is the convex side. As discussed in greater detail below, the present invention also contemplates flexing in the lateral plane.

The present invention finds particular utility in connection with arthroscopic repair and reconstruction of the ligaments of knee, particularly anterior cruciate ligament (ACL) and the posterior cruciate ligament (PCL). The ligaments in the knee connect the femur (thighbone) to the tibia (shin bone), and include the following:

the anterior cruciate ligament (ACL);
the posterior cruciate ligament (PCL);
the medial collateral ligament (MCL); and
the lateral collateral ligament (LCL).

The ACL is one of a pair of cruciate ligaments (the other being the posterior cruciate ligament), also called cruciform ligaments as they are arranged in a crossed formation. The ACL provides 85% of the restraining force to anterior tibial displacement at 30 degrees and 90 degrees of knee flexion. The ACL originates from deep within the notch of the distal femur. Its proximal fibers fan out along the medial wall of the lateral femoral condyle, one of the two projections on the lower extremity of the femur, the other being the medial condyle. There are two bundles of the ACL—the anteromedial (located in the front and toward the middle) and the posterolateral (located behind and to one side, specifically to the outer side), named according to where the bundles insert into the tibial plateau, a critical weight-bearing region on the upper extremity of the tibia. The ACL attaches in front of the intercondyloid eminence of the tibia (a region composed of the medial and lateral intercondylar tubercle that divides the intercondylar area into an anterior and posterior area), being blended with the anterior horn of the medial meniscus.

The PCL connects the posterior intercondylar area of the tibia to the medial condyle of the femur and gets its name by attaching to the posterior portion of the tibia. This configuration allows the PCL to resist forces pushing the tibia posteriorly relative to the femur. The PCL is located within the knee joint where it stabilizes the articulating bones, particularly the femur and the tibia, during movement. It originates from the lateral edge of the medial femoral condyle and the roof of the intercondyle notch then stretches, at a posterior and lateral angle, toward the posterior of the tibia just below its articular surface.

Both the ACL and the PCL are designated as an "intracapsular ligaments" because they lie deep within the knee joint. Both are isolated from the fluid-filled synovial cavity, with the synovial membrane wrapped around them.

As discussed above, when a tissue, more particularly a soft connective tissue in a joint space, becomes damaged or torn from its associated bone or cartilage, surgery is usually required to reattach the tissue or reconstruct the bone. The present invention is directed to select means and mechanisms for securing a torn, damaged or displaced tissue, such as a ligament or a tendon, to the boney tissue associated therewith, such as the femur, knee or tibia.

As used herein, the term "tissue" refers to biological tissues, generally defined as a collection of interconnected cells that perform a similar function within an organism. Four basic types of tissue are found in the bodies of all animals, including the human body and lower multicellular organisms such as insects, including epithelium, connective tissue, muscle tissue, and nervous tissue. These tissues make up all the organs, structures and other body contents. While the present invention is not restricted to any particular soft tissue, aspects of the present invention find particular utility in the repair of connective tissues such as ligaments or tendons, particularly those of the knee joint and shoulder.

In a similar fashion, while the present invention is not restricted to any particular boney tissue, a term used herein to refer to both bones and cartilage, aspects of the present invention find particular utility in the repair or reattachment of connective tissues to the boney elements of the leg and shoulder.

When the damaged tissue is of sufficient quantity and quality, the damaged portion may simply be directly reattached to the bone from which it was torn so that healing back to the bone can take place. However, in other situations, a "graft" may be needed to stimulate regrowth and permanent attachment. In the context of the present invention, the term "graft" refers to any biological or artificial tissue being attached to the boney tissue of interest, including:

Autografts, i.e., grafts taken from one part of the body of an individual and transplanted onto another site in the same individual, e.g., ligament graft;
Isografts, i.e., grafts taken from one individual and placed on another individual of the same genetic constitution, e.g., grafts between identical twins;
Allografts, i.e., grafts taken from one individual placed on genetically non-identical member of the same species; and
Xenografs, i.e., grafts taken from one individual placed on an individual belonging to another species, e.g., animal to man.

Autografts and isografts are usually not considered as foreign and, therefore, do not elicit rejection. Allografts and xenografts are recognized as foreign by the recipient thus carry a high risk of rejection. For this reason, autographs and isografts are most preferred in the context of the present invention.

Surgical interventions such as contemplated herein generally require the boney tissue to be prepared for receiving the graft. In the context of the present invention, such preparation includes the formation of a "socket" or "tunnel", i.e., a hole punched or drilled into the bone into which a graft-associated fixation mechanism, such as an interference screw or suture implant, may be received. In the context of the present invention, the terms "socket" and "tunnel" may be used interchangeably or, alternatively, the term "socket" may be used to refer to a single, preferably interior-opening hole or hollow whereas the term "tunnel" may be used herein to refer to a "through-and-through" passage having both interior and exterior openings. The socket or tunnel may be prepared at the desired target location using conventional instruments such as drills, taps, punches or equivalent hole-producing devices. In the context of the present invention, the femoral "tunnel" is preferably formed from the "inside out" rather than the "outside in".

While certain procedures contemplate directly attaching the graft to the bone, the more common route involves the employment of an implant specially configured to hold and/or enable attachment of the graft to the boney tissue. As used herein, the term "implant" refers to a prosthetic device fabricated from a biocompatible and/or inert material. In the context of the present invention, examples of such "implants" include conventional and knotless anchors of both the screw-threaded and interference-fit variety.

The present invention makes reference to insertion devices commonly referred to in the art as "drills" and "drivers", i.e., devices that "drill" the tunnel and "drive" the graft and/or fixation device into the tunnel. In the context of the present invention, the drills and drivers may be conventional, e.g., rigidly linear as previously herein described, such as for use in the context of a tibal tunnel, or, as discussed in detail herein, "off-axis", e.g., having an angularly offset distal portion adapted to drill off-axis femoral tunnels such as described in detail above.

In the context of the present invention, reference is made to various lock-and-key type mating mechanisms that serve to establish and secure the axial and rotational arrangement of various concentric or relatively slidable device components. It will be readily understood by the skilled artisan that the position of the respective coordinating elements (e.g., recessed slots and grooves that mate with assorted projecting protrusions, protuberances, tabs and splines) may be exchanged and/or reversed as needed.

In certain embodiments, the present invention contemplates securing a graft to an tunnel or a tunnel implant via sutures. In the context of the present invention, the term "suture" refers to a thread-like strand or fiber used to hold body tissues after surgery. Sutures of different shapes, sizes, and thread materials are known in the art and the present invention is not restricted to any particular suture type. Accordingly, in the context of the present invention, the suture may be natural or synthetic, monofilament or multifilament, braided or woven, permanent or resorbable, without departing from the spirit of the invention.

The instant invention has both human medical and veterinary applications. Accordingly, the terms "subject" and "patient" are used interchangeably herein to refer to the person or animal being treated or examined. Exemplary animals include house pets, farm animals, and zoo animals. In a preferred embodiment, the subject is a mammal, more preferably a human.

Hereinafter, the present invention is described in more detail by reference to the Figures and Examples. However, the following materials, methods, figures, and examples only illustrate aspects of the invention and are in no way intended to limit the scope of the present invention. For example, while the present invention makes specific reference to arthroscopic procedures, it is readily apparent that the teachings of the present invention may be applied to other minimally invasive procedures and are not limited to arthroscopic uses alone. As such, methods and materials similar or equivalent to those described herein can be used in the practice or testing of the present invention.

EXAMPLES

FIGS. 1 through 9 depict the inner drive assembly 100 for an endoscopic drilling device 300 of the present invention. Inner drive assembly 100 includes an elongate drive rod 102 that has at its proximal end a hub assembly that includes inner hub 124, spring retainer 126 and spring 128. Mounted to the distal end drive rod 102 is drilling member 104. Drilling member 104 is made up of a distal portion 106 that takes the form of a twist drill bit and a cylindrical mid portion 108 that terminates in proximal portion 110. Distal portion 103 of drive rod 102 has a distal-most portion 112 having cylindrical distal recess 105 formed therein that is sized to receive proximal portion 110 of drilling member 104, such that when proximal portion 110 is positioned in distal recess 105 of drive rod 102, concentricity of the respective elements is established. Thereafter, distal portion 103 may be affixed to drilling member 104, preferably by laser welding, though other joining methods are contemplated. Bushing 116 and washer 118 are rotatably positioned on cylindrical portion 108 of drilling member 104. Thereafter, stop collar 114 is positioned on cylindrical portion 108 of drilling member 104 and secured by laser welding or other suitable equivalent means. Stop collar 114 is positioned a short distance away from the proximal end of bushing 116 so as to allow drilling member 104 to rotate freely in bushing 116 while simultaneously preventing axial movement of drilling member 104 relative to bushing 116. In a preferred embodiment, bushing 116 is formed from a suitable polymeric material including, but not limited to, polyetheretherketone (PEEK), a polymeric composite such as, for instance, carbon fiber reinforced PEEK (PEEK CF). In other embodiments, bushing 116 may be formed from a suitable metallic material.

As best seen in FIGS. 5 through 9, the proximal end of drive rod 102 forms a proximally extending cylindrical portion 134 on which are formed opposed flats so that torque supplied by a driving element to inner hub 124 may be transferred to drive rod 102. Critically, the axial position of hub 124 on drive rod 102 is not fixed. Rather, hub 124 is slidably positioned on portion 134, with the limits of axial travel being limited by shoulder 139 of drive rod 102, as well as by proximal stop collar 138 that is affixed to the proximal end of portion 134 of drive rod 102 after hub 124 has been positioned thereon.

Figure 10:
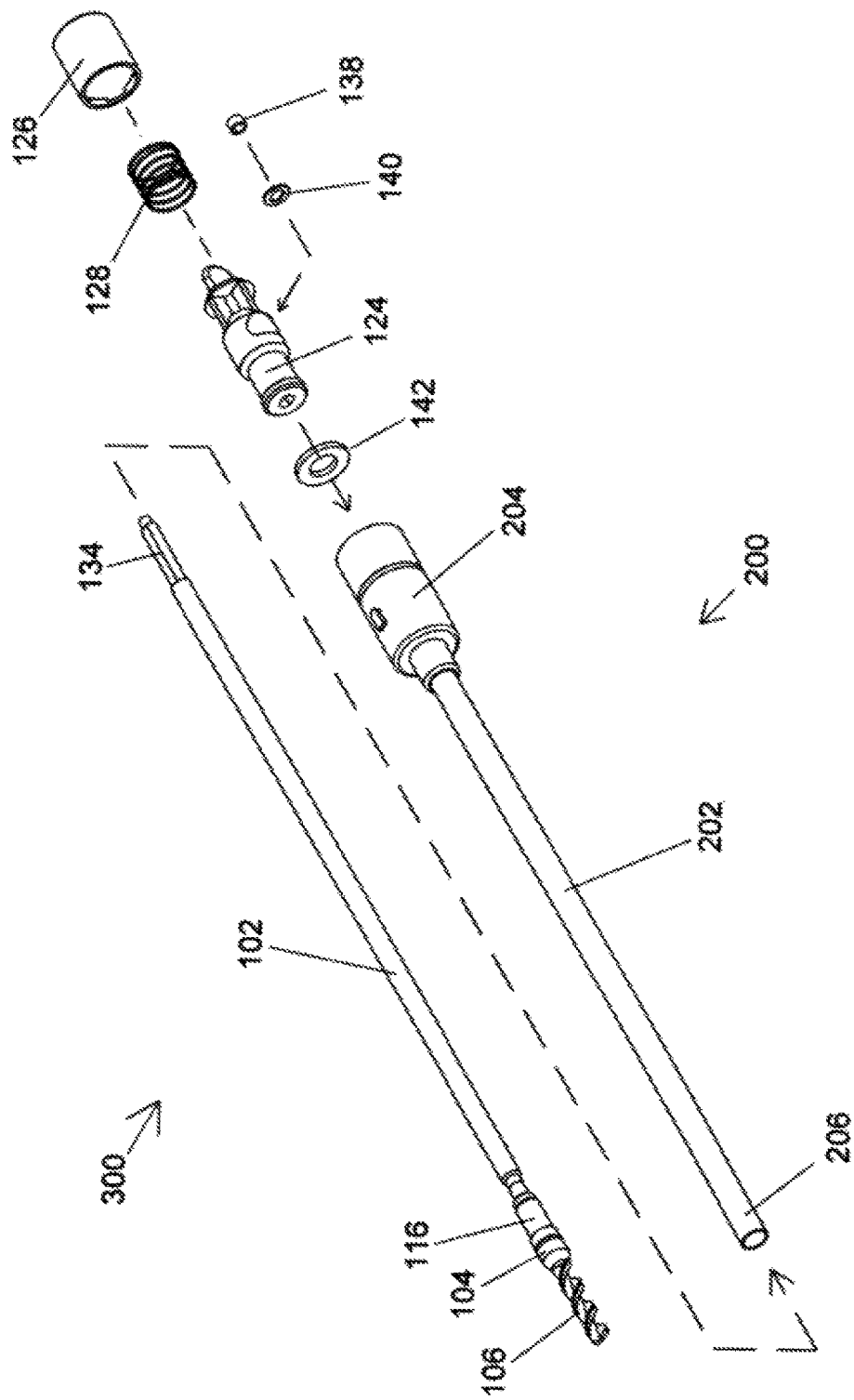
FIG. 10 is an exploded assembly view of the elements of an endoscopic drilling device of the present invention.
Figure 11:
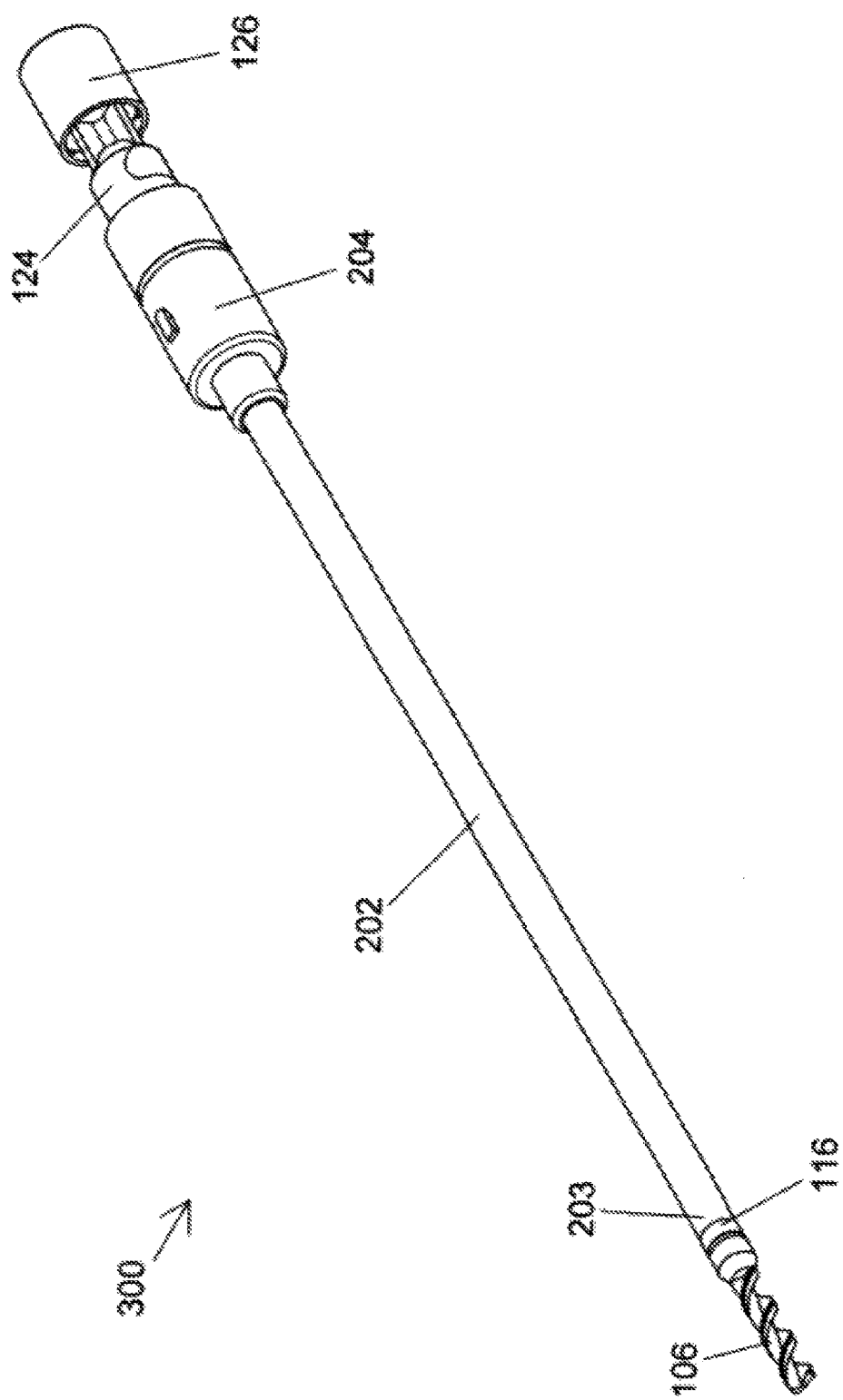
FIG. 11 is a perspective view of the elements of FIG. 10 assembled to form an endoscopic drilling device of the present invention.
Figure 12:
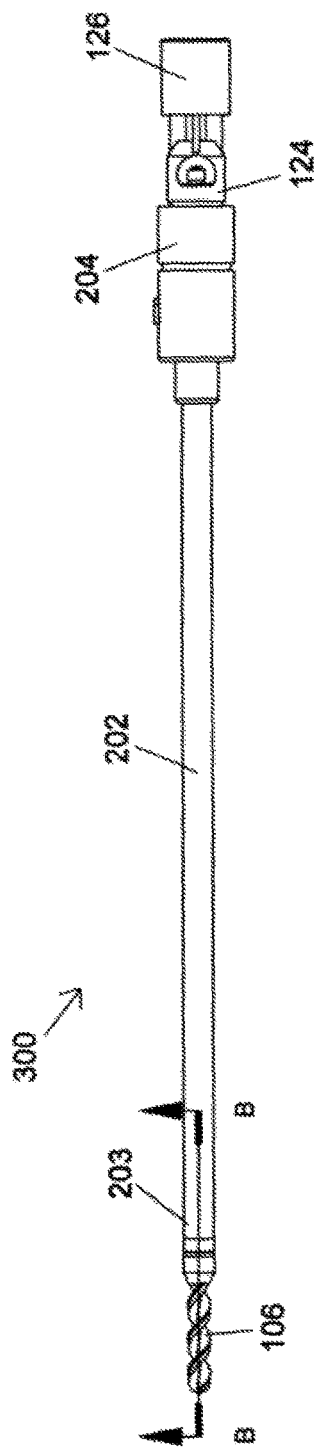
FIG. 12 is a plan view of the objects of FIG. 11.
Figure 13:
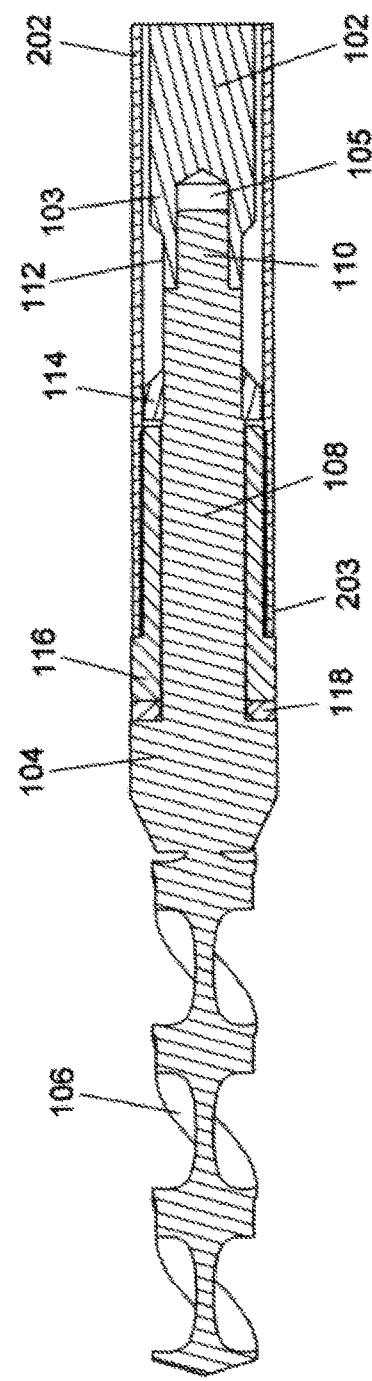
FIG. 13 is a sectional view of the distal portion of the objects of FIG. 12 at location B-B.

FIG. 10 depicts an exploded assembly of an endoscopic drilling device 300 of the present invention. Outer assembly 200 has an elongate tubular portion 202 with outer hub 204 affixed to its proximal end, and with a distal end 206. Inner assembly 100 is assembled to outer assembly 200 in the following manner. The components of the inner assembly, including drilling member 104, bushing 116, stop collar 114 and drive rod 102 (FIGS. 1 through 9), is inserted into distal end 206 of tubular member 202 of outer assembly 200, with bushing 116 being pressed into distal end 206 of tubular member 202 as best seen in FIG. 13. The interference between bushing 116 and tubular member 202 is sufficient to prevent axial movement between the mating elements. In embodiments wherein bushing 116 is formed of a metallic material, bushing 116 may be secured to distal end 206 of tubular member 202 by laser welding, crimping or other suitable mechanical attachment means. Thereafter thrust washer 142 is inserted into the proximal end of outer hub 204 and inner hub 124 is assembled to proximal portion 134 with washer 140 and proximal stop ring 138. Spring 128 is then inserted into spring retainer 126 and spring retainer 126 is snapped onto the proximal end of inner hub 124.

Referring to FIGS. 11 through 15, which depict the assembled device 300 of the present invention, the axial position of drive rod 102 and drilling element 104 affixed thereto is established by bushing 116, which is irremovably affixed to the distal end 203 of outer tubular element 202. The axial position of inner hub 124 relative to outer hub 204 is established by thrust washer 142 which is positioned between the distal-most surface of inner hub 124 and proximally facing surface 205 of outer hub 204. Contact is maintained between the surfaces by force exerted on inner hub 124 by spring 128, the proximal end of spring retainer 126 and spring 128 contained therein engaging a shoulder on the driving shaft of the endoscopic shaver handpiece, into which device 300 is inserted. Referring again to FIG. 15, inner hub 124 transmits torque to drive rod 102 via proximal portion 134 and flats formed thereon (see FIG. 6), but is slidably assembled thereto. The limit of axial motion of inner hub 124 relative to drive rod 102 is established by proximal surface 139 of drive rod 102 and by washer 140 and proximal stop ring 138. In a preferred embodiment, thrust washer 142 is formed of a suitable polymeric material, such as PEEK. In other embodiments a metallic material may be used.

Figure 16:
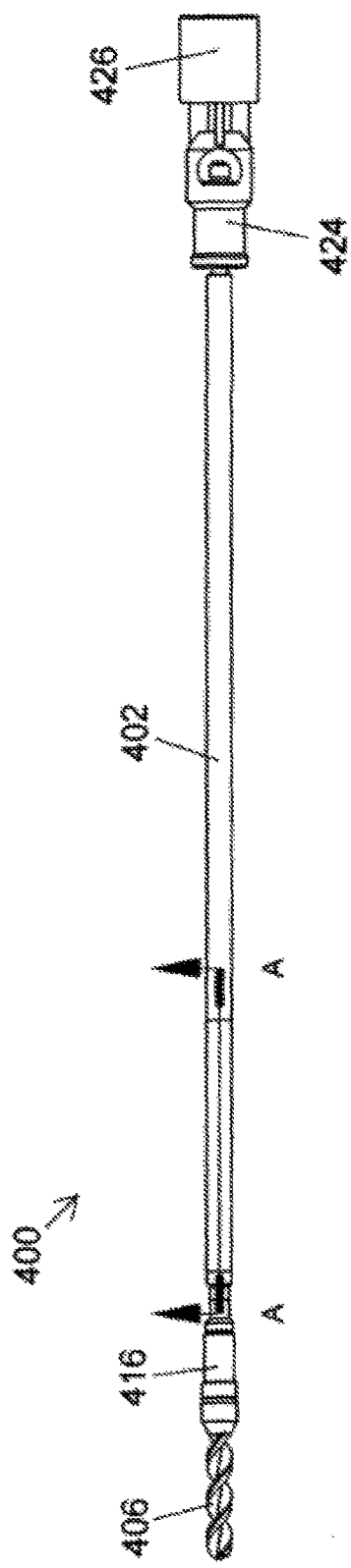
FIG. 16 is a plan view of the inner drive assembly of an alternate embodiment endoscopic drilling device of the present invention.
Figure 17:
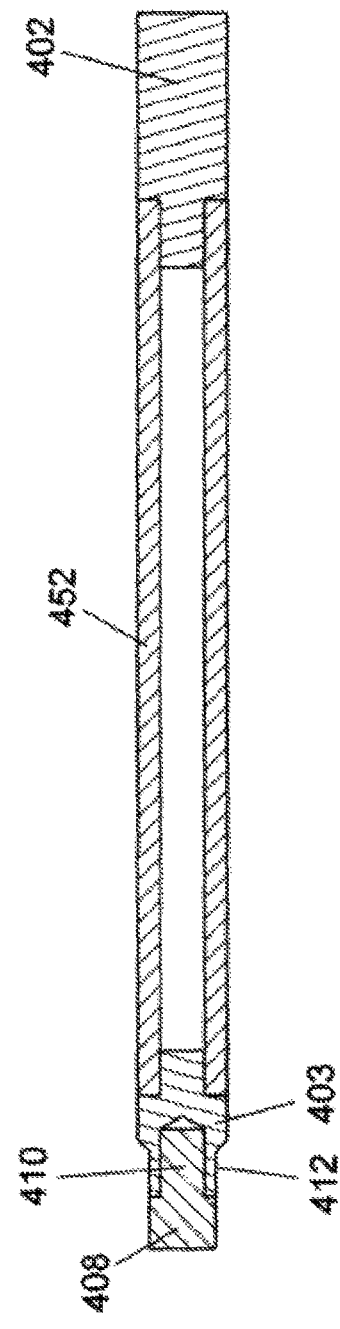
FIG. 17 is a sectional view of the objects of FIG. 16 at location A-A.
Figure 18:
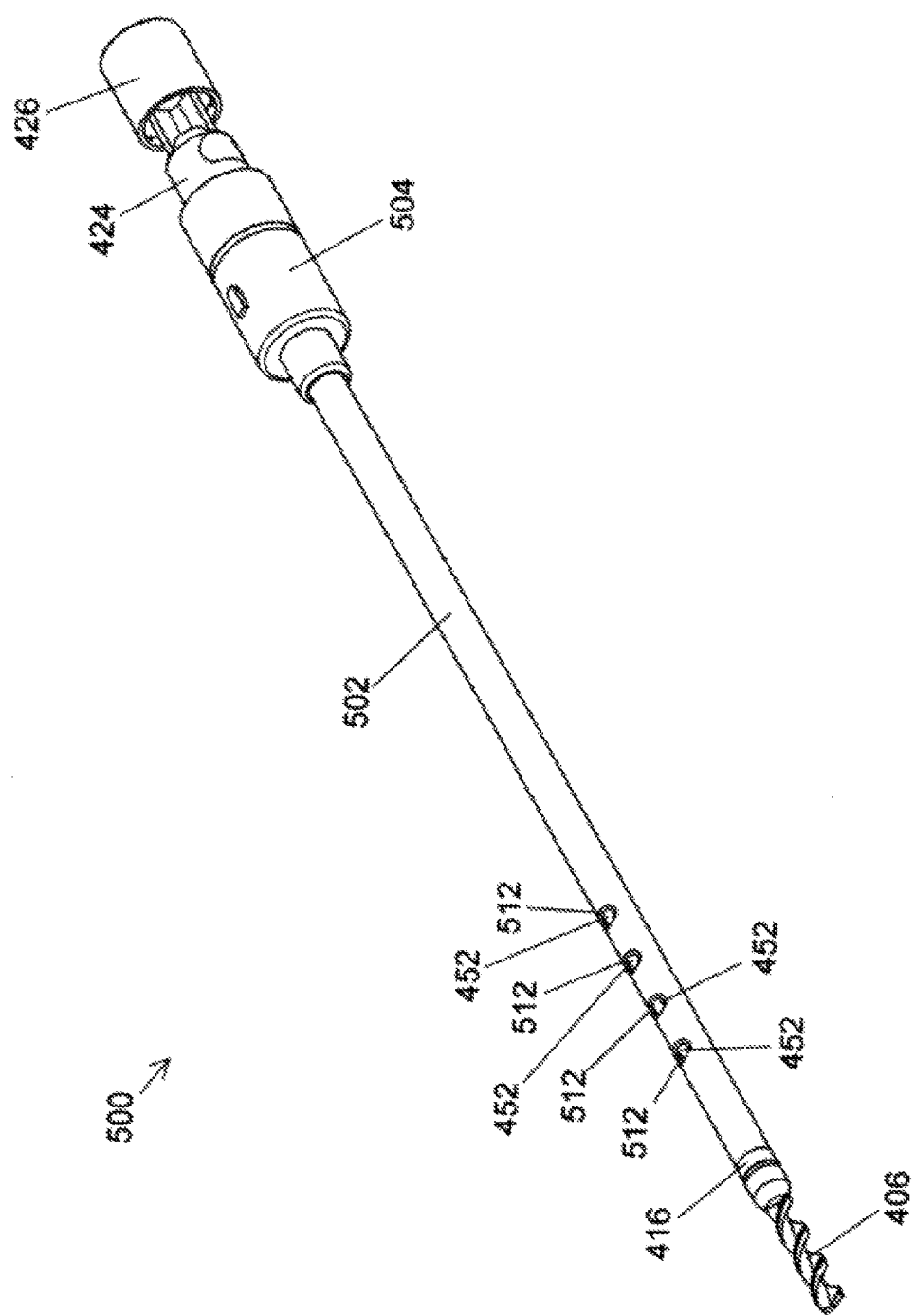
FIG. 18 is a perspective view of an alternate embodiment endoscopic drilling device incorporating the inner drive assembly of FIG. 16.
Figure 19:
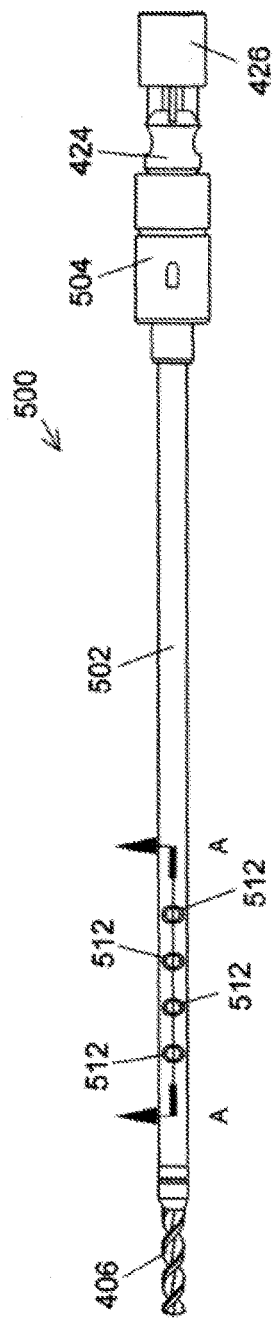
FIG. 19 is a plan view of the objects of FIG. 18.
Figure 20:
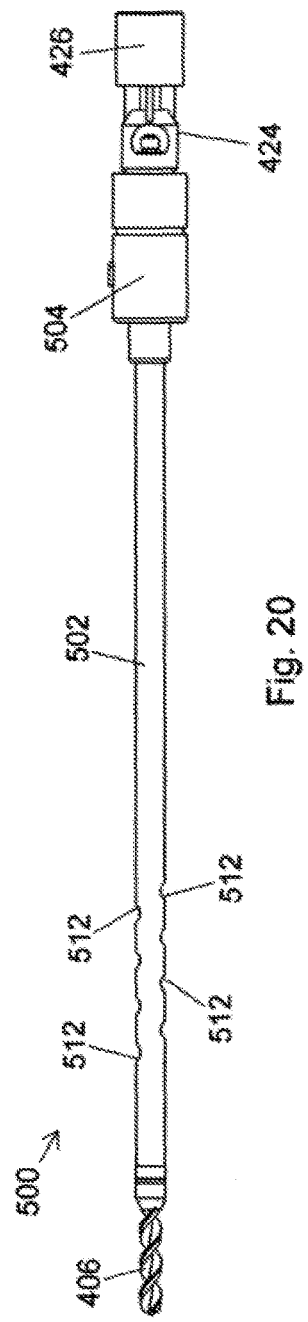
FIG. 20 is a side elevational view of the objects of FIG. 18.

In other embodiments, the distal portion of the endoscopic drilling device of the present invention may be angularly offset from the proximal, torque-transmitting portion of the device. The inner assembly 400 for an exemplary embodiment of such an offset configuration is depicted in FIGS. 16 and 17. Inner assembly 400 is identical to inner assembly 100 (FIGS. 1 through 9) in all aspects of form and function except as specifically described hereafter. Specifically, unlike drive rod 102, drive rod 402 is not of unitary construction but rather has a distally located portion, which is a torque-transmitting flexible element 452. Flexible element 452 is affixed to the proximal portion of drive rod 402, and to distal portion 403 of drive rod 402 by soldering, welding, brazing or mechanical means.

Figure 21:
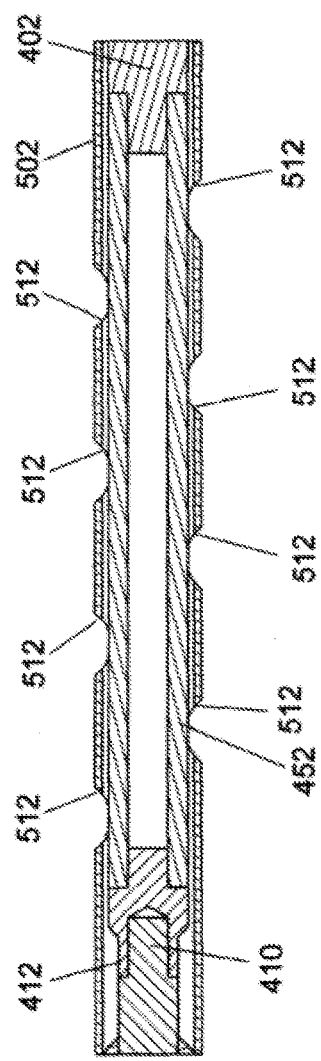
FIG. 21 is an expanded sectional view of the objects of FIG. 19 at location A-A.
Figure 22:
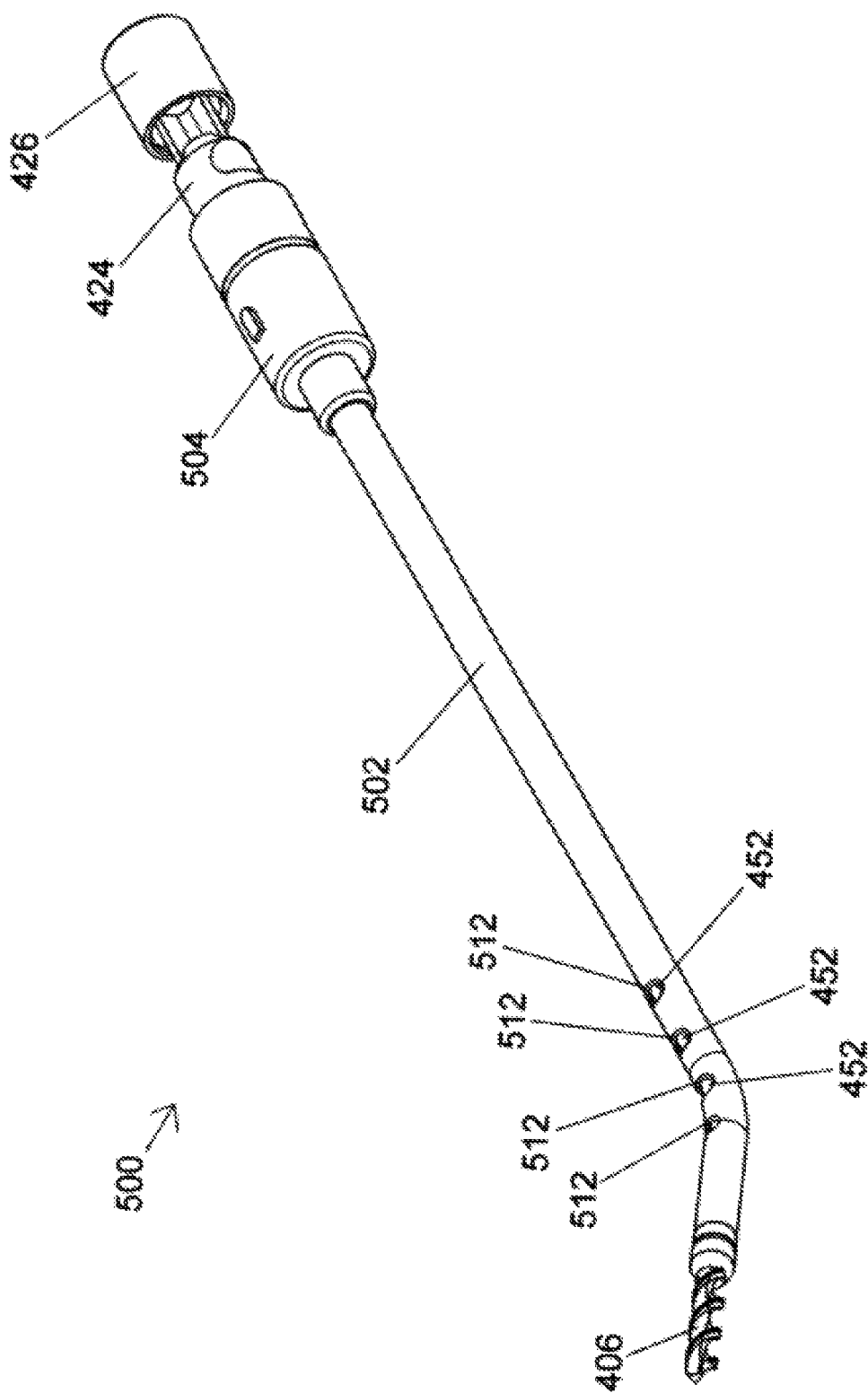
FIG. 22 is a perspective view of the endoscopic shaver device of FIG. 18 with the distal portion angularly offset from the proximal, torque transmitting portion.
Figure 23:
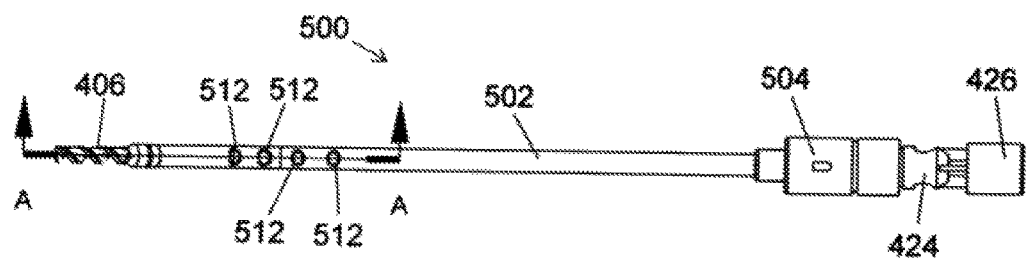
FIG. 23 is a plan view of the objects of FIG. 22.
Figure 24:
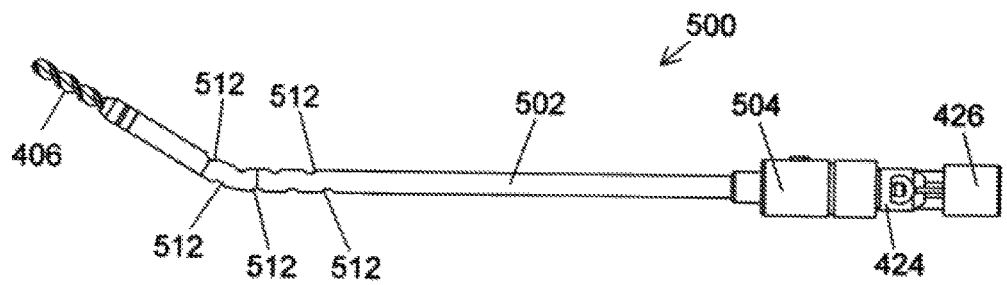
FIG. 24 is a side elevational view of the objects of FIG. 23.

FIGS. 18 through 21 depict an embodiment of the present invention in which the distal portion may be angularly offset from the proximal portions of the device. Endoscopic drilling device 500 is alike in all aspects of form and function to device 300 (FIGS. 11 through 15) except as specifically described hereafter. Device 500 substitutes inner assembly 400 (FIGS. 16 and 17) for inner assembly 100 (FIGS. 3 through 9). Tubular member 502 is substituted for tubular member 202 (FIGS. 10 through 15). In a preferred embodiment, tubular member 502 has formed in its distal region notches 512 that extend from the tube's outer surface through the wall to the inner surface. Notches 512 allow bending of tubular member 502 with the bend being localized in the region of notches 512. Notches 512 allow deformation of tubular member 502 in the region of notches 512 with minimal reduction in the diameter of the flexible member that may be inserted therein. Without notches 512, bending of tubular member 502 causes the cross-section of tubular member in the region of the bend to become oval with the height of the oval determining the diameter of the flexible element, which can be rotatably positioned therein. To minimize this ovality, large bend radii must be used. The presence of notches 512 in the radially inner and outer wall portions of tubular member 502 locally removes the resistance to bending due to these portions of tube wall. This allows tubular member 502 to not only be bent to a first angular offset, but to be re-bent to a second or even third offset with all of the bends occurring in the region of notches 512 in which the flexural strength of tubular member 502 has been locally reduced. Without notches 512, bending tubular member 502 to a first angular offset causes work hardening of the material in the region of the bend. Modification of the angular offset by re-bending tubular member 502 when notches 512 are not present will result in bending of tubular member 502 adjacent to the existing bend rather than in the region of the existing bend since the material in this bend region has been work hardened. However, in some embodiments of the present invention in which a bend is formed in tubular member 502 at the time of manufacture and no further modification of the bend is intended, notches 512 may be absent. As best seen in FIG. 21, notches 512 are formed in a region of tubular member 502 that is adjacent to flexible member 452 of drive rod 402.

Figure 25:
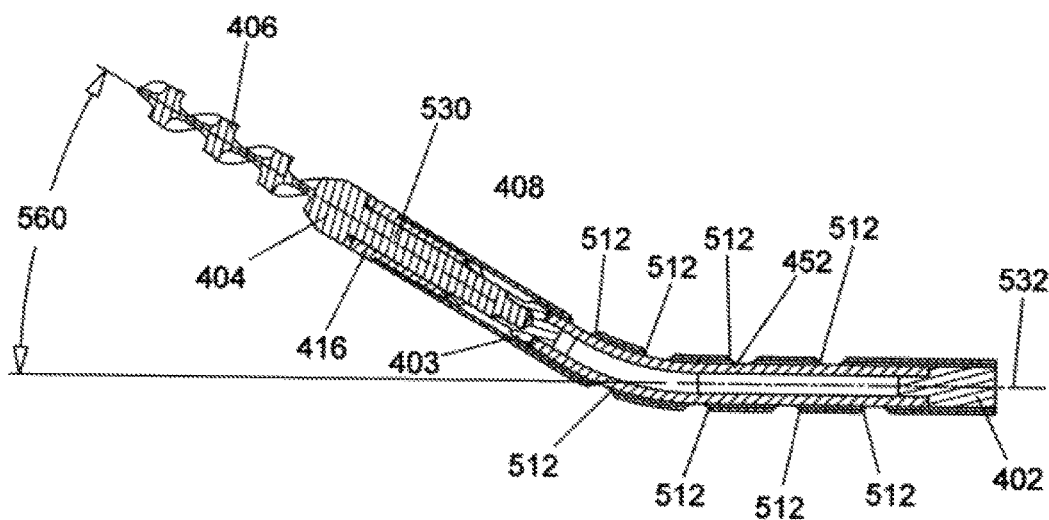
FIG. 25 is a expanded sectional view of the objects of FIG. 23 at location A-A.

FIGS. 22 through 25 depict endoscopic drilling device 500 with the distal portion of device 500 angularly offset from its more proximal portions. Referring to FIG. 25, axis 530 of the distal portion of device 500 is offset angle 560 from axis 532 of the proximal portion of device 500. The bend in outer tubular member 502 has its distal limit in the distal portion of the region of notches 512 and is centered proximally thereto. As angle 560 is increased, the centering of the bend region moves proximally toward the midpoint of the region of notches 512. The change of the cross-section of tube 502 in the region of the bend is determined by the radius of the bend, and by the number, spacing and geometry of notches 512. These variables must be optimized to allow flexible drive portion 452 of drive rod 402 to rotate freely in the bend region.

Figure 26:
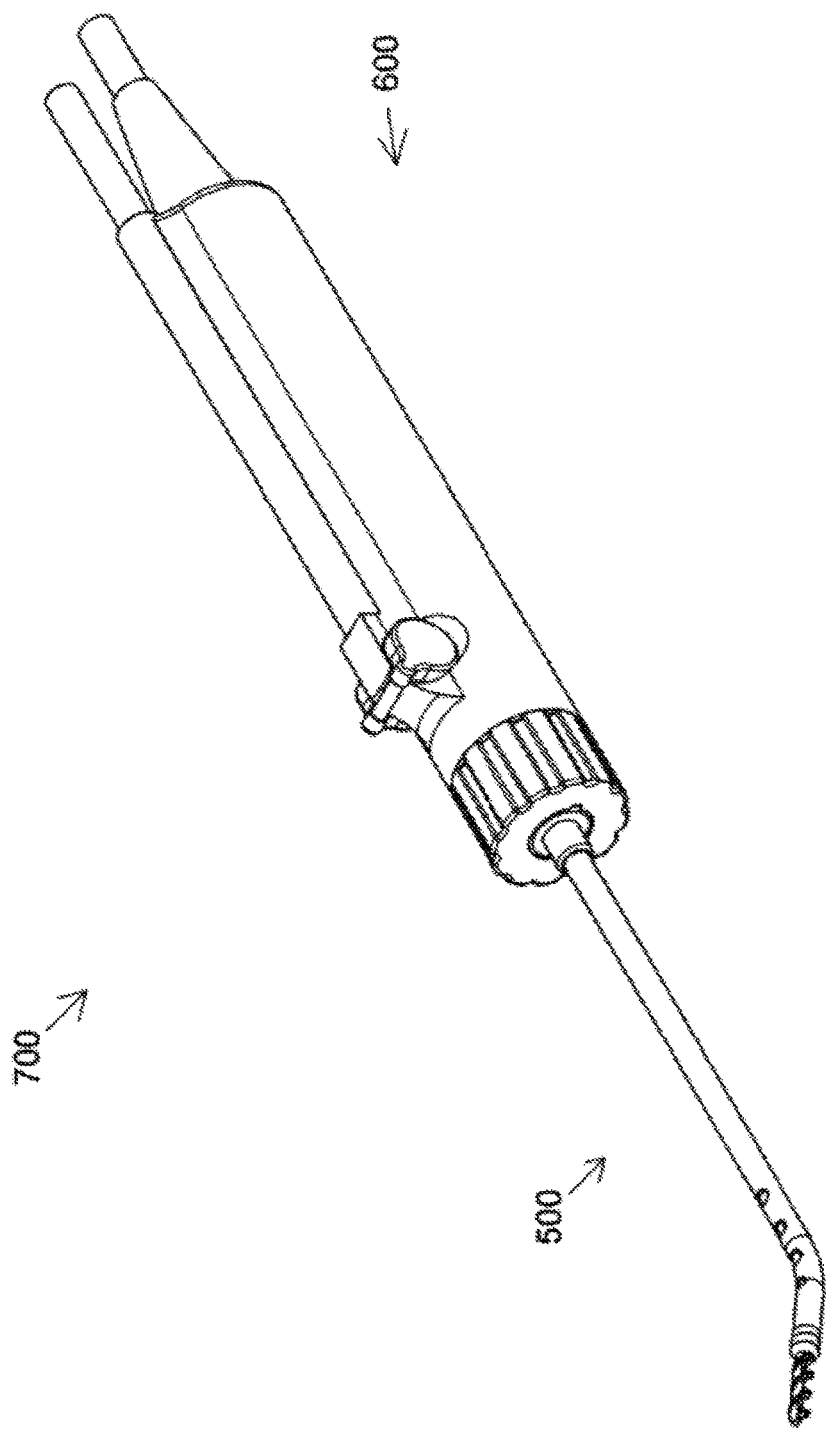
FIG. 26 is a perspective view of the endoscopic shaver device of FIGS. 22 through 26 mounted in an endoscopic shaver handpiece.
Figure 27:
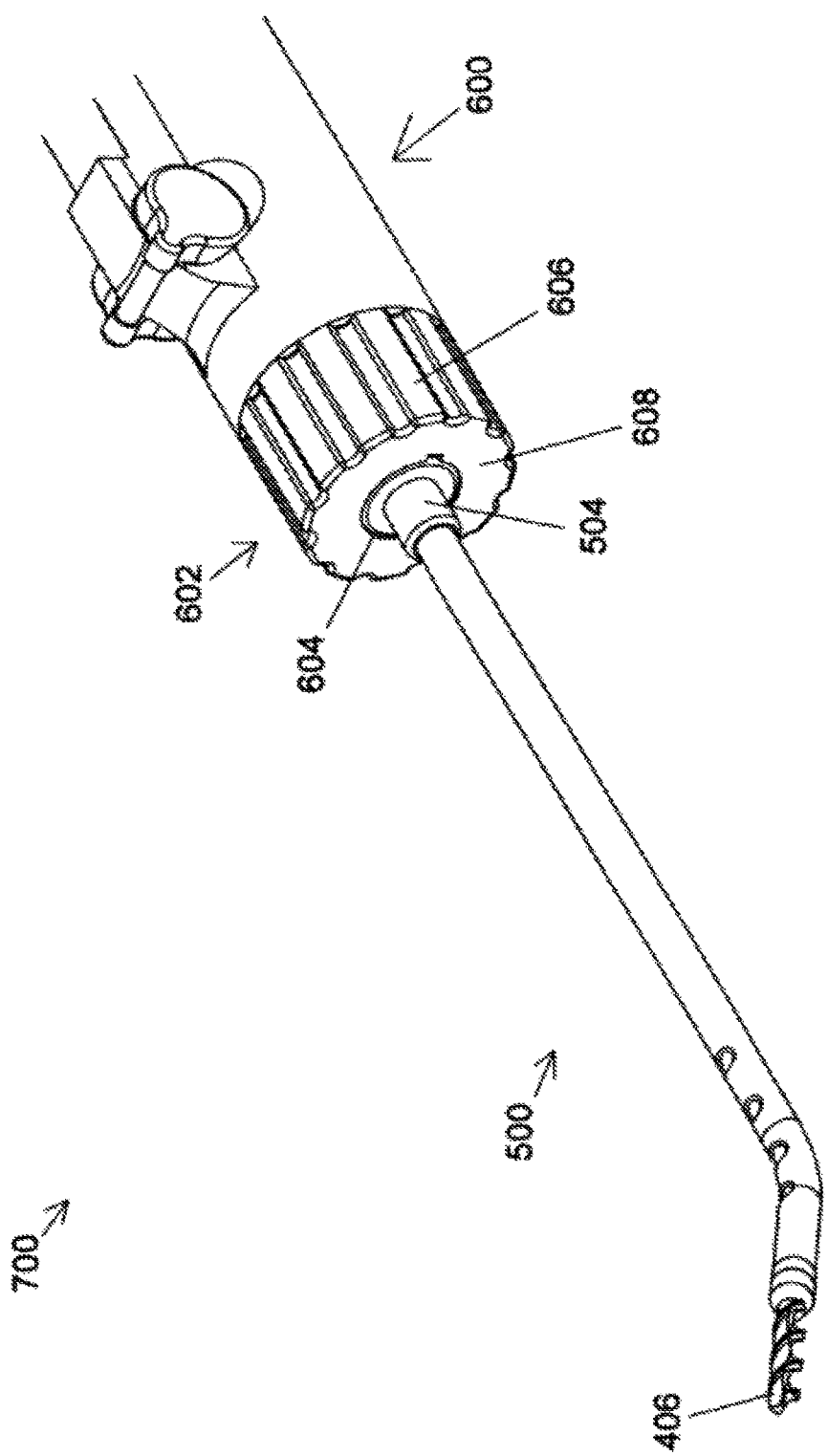
FIG. 27 is an expanded view of the distal portion of the objects of FIG. 26.

Device 500 may be removably mounted in an endoscopic shaver handpiece 600 as depicted in FIGS. 26 and 27 to form endoscopic drilling system 700. Shaver handpiece 600 has a distal end 602 that has rotatably mounted thereto collar 606 which is rotatable between a first position in which aligned keyways allow insertion of the outer hub 504 into a distal cylindrical recess, and a second position in which a keyway in collar 606 is angularly displaced from a second keyway so as to prevent removal of outer hub 504 from handpiece 600. Inner hub 424 (not shown) is engaged with the drive shaft of handpiece 600 so as to transmit torque from handpiece 600 through the inner assembly of device 500 to distal drilling element 406. Outer hub 504 is confined within a distal recess of handpiece 600, the intersection of the distal recess and distal surface 608 of distal collar 606 forming edge 604. Shaver handpiece 600 is connected via a cable to a control console (not shown) that allows the surgeon to select a rotational speed appropriate for the size and location of the socket to be drilled.

When using a powered endoscopic drilling device of the present invention to place an anchoring implant such as described in Dougherty's U.S. Pat. No. 9,226,817 referenced above in a suitable boney surface, the surgeon first identifies the location at which a socket is to be drilled, and then determines the optimal angular orientation of the socket. Next, the surgeon determines the degree of angular offset required between the axis of the drilling device distal portion and the axis of shaver handpiece 600 to achieve the desired placement and angular orientation of the socket. When using embodiments of the present invention in which the angular offsets are preset by the manufacturer and cannot be modified, the surgeon may choose from a selection of devices having a range of angular offsets a drilling device with an angular offset most closely matching the determined optimal degree of offset. Alternatively, when using embodiments of the present invention that are rebendable by the surgeon in the operating room, the surgeon may use a bending device to impart the desired angular offset to the drilling device. The surgeon may modify the degree of offset as required to achieve optimal placement and angular orientation of the socket. When the surgeon is satisfied with the angular offset of the distal portion relative to the handpiece axis, the socket is drilled. In certain circumstances, as when using a large diameter drilling element, it may be desirable to first drill a shallow, smaller diameter hole in the location prior to drilling with the larger drill to ensure that the larger drill does not stray from the desired location at the start of drilling. Because endoscopic drilling devices of the present invention are scalable, both drilling devices may be constructed in accordance with the principles of the present invention.

As noted above, the powered endoscopic drilling devices of the present invention may also be used for a microfracture procedure, wherein one or more holes in a prepared boney surface. In such cases, an exemplary method would typically include the steps of (a) providing a powered device for producing holes in a prepared boney surface, wherein the device has a distal portion having an axis formed to a first initial angle with respect to the proximal portion of the device, and is formable to at least a second angle to the proximal portion by the surgeon during preparation for use; (b) mounting the device in an arthroscopy shaver handpiece; (c) determining the optimum angle of the distal portion so as to produce at least one hole having an axis substantially normal to the prepared surface; (d) if necessary, optionally bending the distal portion of the device to the optimum angle; (e) forming the hole in the bone surface; and (f) repeating steps (c) through (e) as necessary to form a desired pattern of holes.

Referring to FIG. 27, outer hub 504 is inserted into and retained in a cylindrical recess in distal end 602 of shaver handpiece 600. To allow this insertion, clearance must exist between the elements. That is, the diameter of the cylindrical recess in distal end 602 of handpiece 600 must be greater than that of outer hub 504. This clearance allows drilling device 500 some degree of angular deflection relative to handpiece 600 since outer hub 504 is not tightly held within the recess. This deflection is inconsequential when using an endoscopic burr or shaver with handpiece 600, since the forces applied to the shaver are small and generally predictably orthogonal to the distal end of the burr or shaver. However, when using a powered endoscopic drilling device of the present invention such as drilling device 500, deflection of the distal end of the device at the start of drilling may be more consequential. Because the distal drilling member 406 may tend to "walk" as the cutting flutes engage bone, clearance between the outer hub 504 and the distal recess may compromise the surgeon's ability to control the process since the surgeon is controlling shaver handpiece 600 rather than the drilling device. There is accordingly a significant need for a means for stabilizing so as to minimize angular deflection of the endoscopic drilling device due to clearance between outer hub 504 and the distal recess of shaver handpiece 600.

Figure 28:
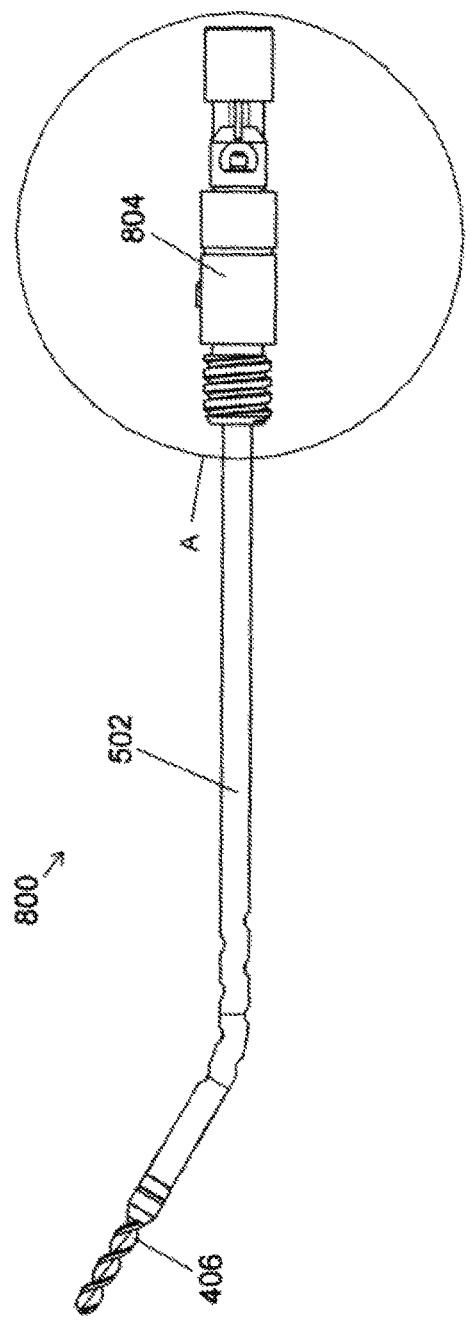
FIG. 28 is a side elevational view of an alternate embodiment endoscopic drilling device of the present invention.
Figure 29:
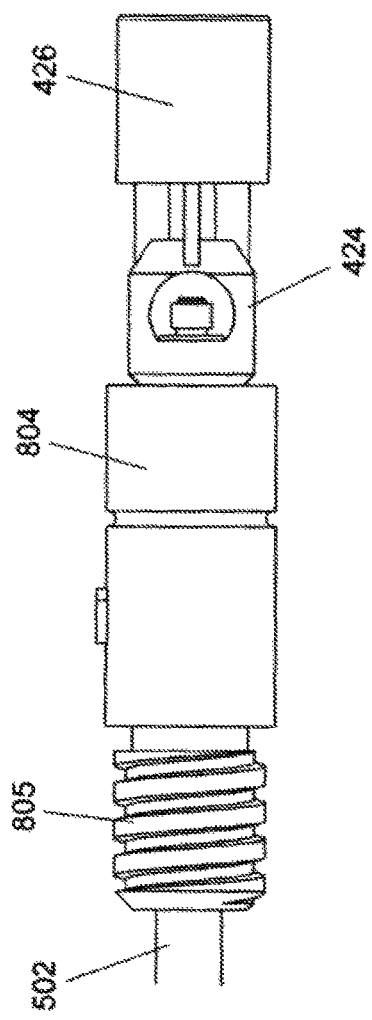
FIG. 29 is an expanded view of the proximal portion of the objects of FIG. 28 at location A.
Figure 30:
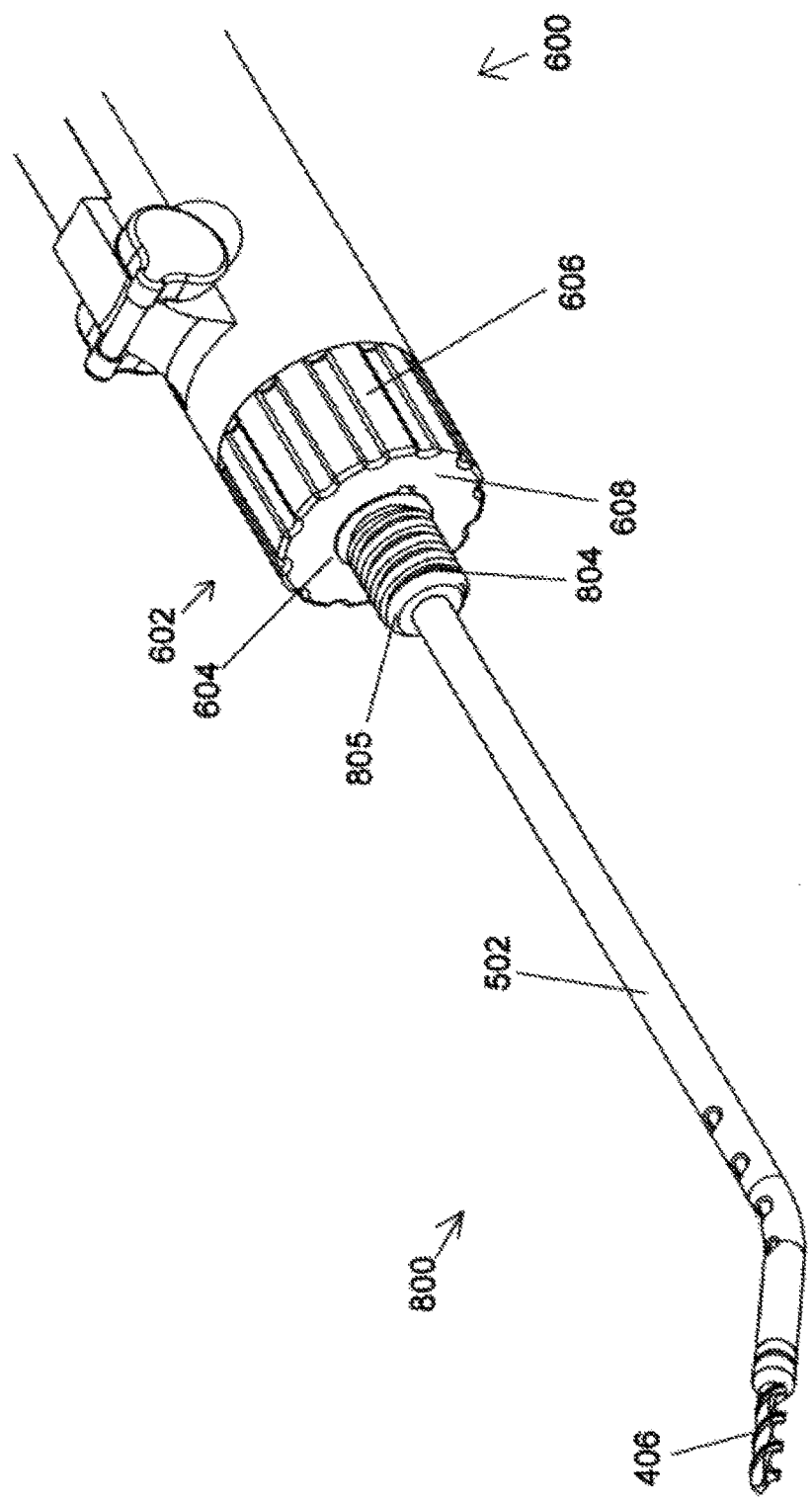
FIG. 30 is a perspective view of the endoscopic drilling device of FIG. 28 mounted in an endoscopic shaver handpiece.

FIGS. 28 and 29 depict an endoscopic drilling device 800 of the present invention that is identical in all aspects of form and function to drilling device 500 except as specifically described hereafter. Specifically, outer hub 504 of drilling device 500 has been replaced with outer hub 804. Outer hub 804 has a threaded distal portion 805. As seen in FIG. 30, when device 800 is mounted in shaver handpiece 600 threaded distal portion 805 protrudes beyond distal surface 608 of collar 606.

Figure 31:
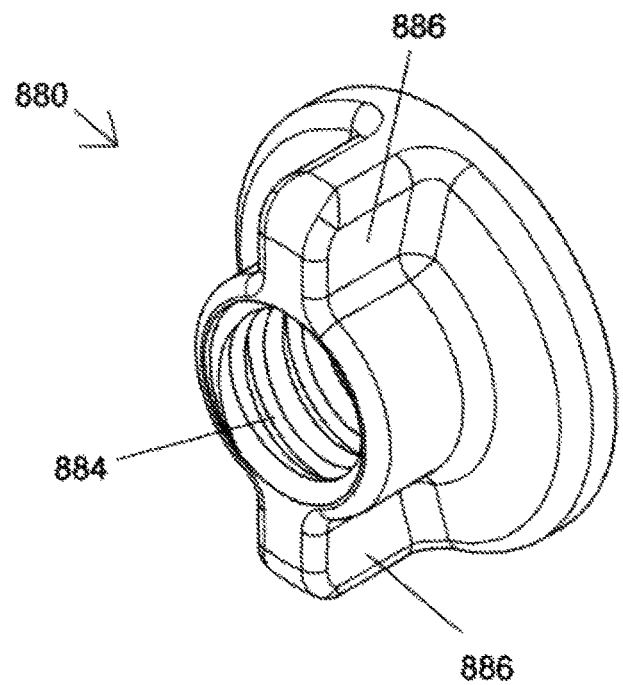
FIG. 31 is a distal perspective view of a threaded stabilizer device for use with the endoscopic drilling device of FIG. 28.
Figure 32:
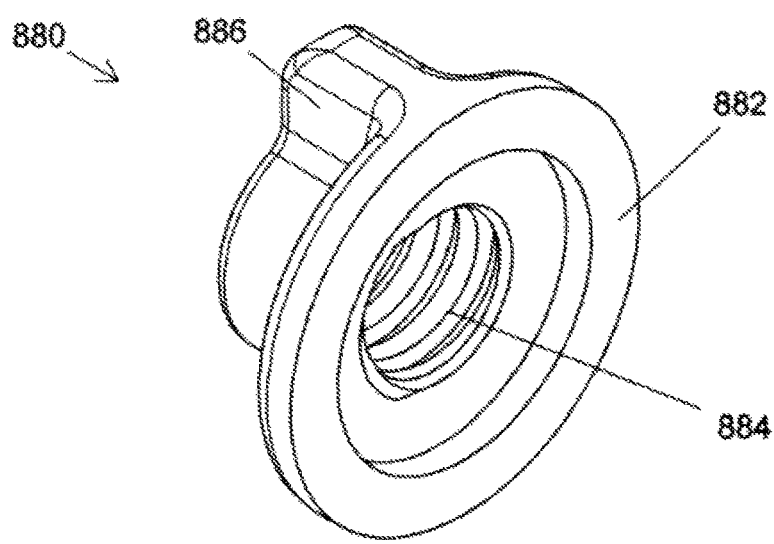
FIG. 32 is a proximal perspective view of the stabilizer device of FIG. 31.

Referring now to FIGS. 31 and 32 depicting a stabilizing device 880, device 880 has a proximal surface 882 and a threaded portion 884. Device 880 also has distally extending, laterally opposed ribs 886. In form and function, stabilizing device 880 is a wing nut, the threaded portion being complementary to distal threaded portion 805 of outer hub 804 of device 800 so that stabilizing device 880 may be threaded onto portion 805.

Figure 33:
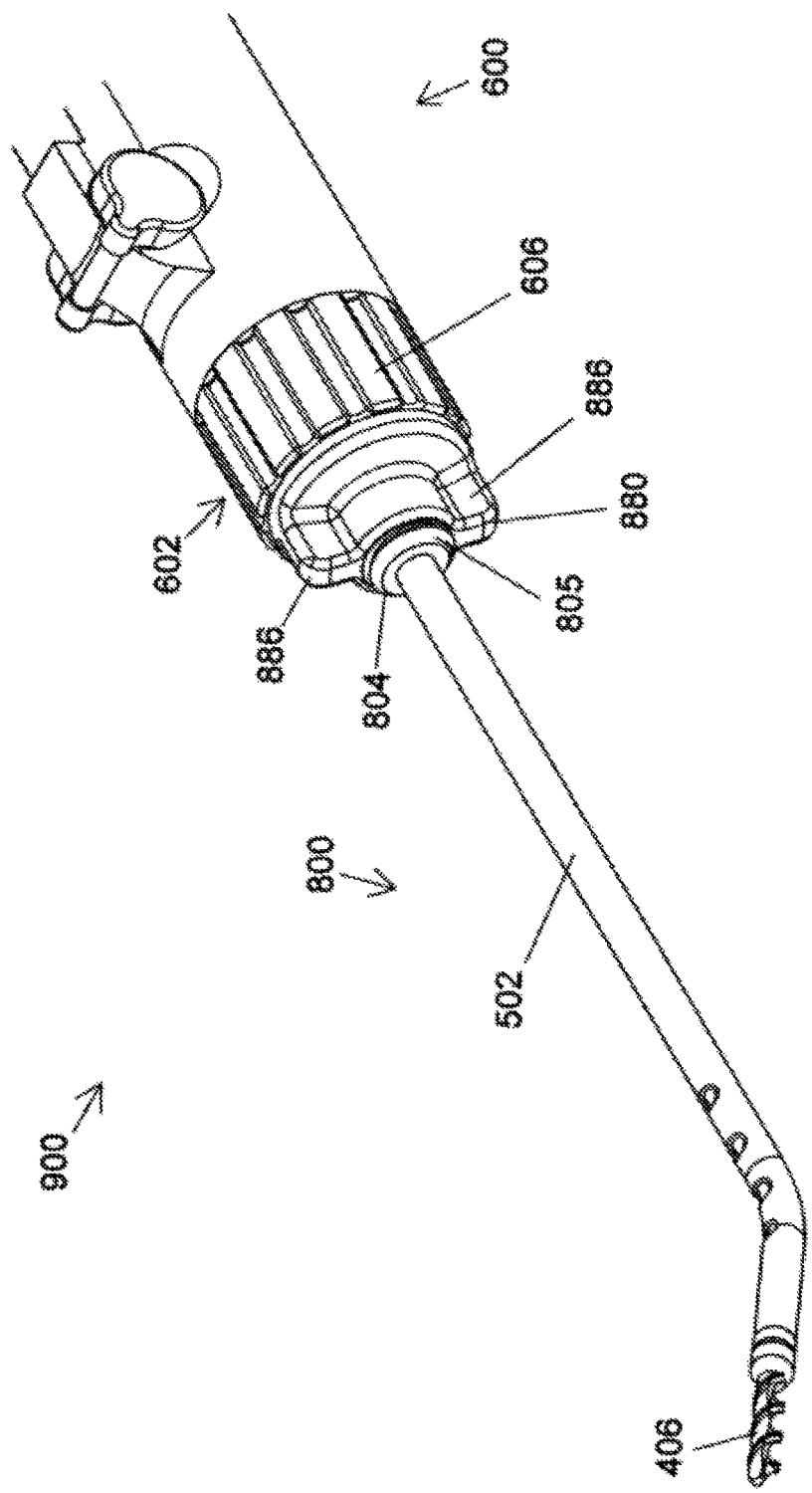
FIG. 33 is a perspective view of the objects of FIG. 30 with the stabilizer device of FIG. 31 mounted to the endoscopic drilling device.

FIG. 33 depicts a drilling system that includes the elements of FIG. 30 but with stabilizing device 880 removably mounted on distal portion 805 of outer hub 804 in preparation for use. Stabilizing device 880 is threaded onto distal portion 805 of outer hub 804 until proximal surface 882 of stabilizing device 880 contacts distal surface 608 of collar 606 of handpiece 600. Thereafter stabilizing device 880 is tightened sufficiently to minimize angular deflection of endoscopic drilling device 800 relative to endoscopic shaver handpiece 600.

Drilling devices of the present invention may be readily powered by a conventional arthroscopy shaver handpiece. In preferred embodiments, the devices are single-use, thereby eliminating the need to clean and sterilize as with standard drilling systems. As noted previously, opportunities for infection due to improper cleaning and sterilization are eliminated.

INDUSTRIAL APPLICABILITY

As noted previously, there is a need in the art for specialized endoscopic drilling devices that may be readily powered by a conventional shaver handpiece and further may be utilized to secure a soft tissue graft to a boney surface. There is further a need in the art for minimally invasive systems and methods that can efficiently form off-axis sockets and/or tunnels in boney surfaces. Embodiments of the present invention meet one or more of those needs. While certain embodiments of the present invention are described as having a rigid linear construction, others are provided with a fixed angular offset between the distal drilling portions of the device and the more proximal portions. Still other embodiments may be constructed such that the distal portion may be angularly offset by the surgeon at the time of use, the angular offset being optimized by the surgeon to suit the procedure to be performed, the devices being bendable and rebendable so that optimal positioning may be maintained throughout, for instance, a microfracture procedure. The angular offset of the distal portion allows surgeons to drill holes in sites inaccessible with standard linear drilling devices.

The disclosure of each publication, patent or patent application mentioned in this specification is specifically incorporated by reference herein in its entirety. However, nothing herein is to be construed as an admission that the invention is not entitled to antedate such disclosure by virtue of prior invention.

The invention has been illustrated by reference to specific examples and preferred embodiments. However, it should be understood that the invention is intended not to be limited by the foregoing description, but to be defined by the appended claims and their equivalents.

What is claimed:

1. An endoscopic surgical assembly comprising:
   a. an elongate tubular outer member having a distal end configured to receive a bushing element, and a proximal end having a first proximal hub assembly mounted thereto, wherein said first proximal hub assembly is configured for removable mounting to an endoscopic shaver handpiece,
   b. an elongate inner member having a distal element, an elongate middle element, a proximal portion and a second proximal hub assembly configured to transfer torque received from an endoscopic shaver handpiece to said elongate middle member, wherein said distal element includes a distal portion configured to drill a hole, further wherein said distal portion comprises a proximal facing planar surface, and an elongate cylindrical proximal portion extending therefrom, wherein said elongate cylindrical proximal portion has a proximal end configured for attachment to said elongate middle element, and
   c. a bushing element mounted to the distal end of said elongate tubular outer member, said bushing element having a cannulation configured to slidably receive said proximal portion of said distal element of said inner member, and planar proximal-most and distal-most surfaces;

wherein said elongate inner member is rotatably positioned within said elongate tubular outer member, said elongate cylindrical proximal portion of said distal element of said elongate inner member being rotatably positioned within said cannulation of said bushing element, and further wherein proximal motion of said inner member relative to said outer member is prevented by cooperative interaction of said proximal planar surface of said distal portion of said distal element of said inner member and said planar distal-most surface of said bushing element.

2. The surgical assembly of claim 1 further comprising a stop element having a planar distal surface positioned on said elongate cylindrical proximal portion and affixed thereto such that distal motion of said inner member is prevented by interaction between said planar distal surface of said stop element and said proximal-most surface of said bushing element.

3. The surgical assembly of claim 1 wherein said proximal hub assembly is axially slidably positioned on said proximal end of said middle portion of said elongate inner member.

4. The surgical assembly of claim 1 wherein a portion of said middle portion of said elongate inner member is a flexible torque-transmitting element.

5. The surgical assembly of claim 4 wherein said elongate tubular outer member has a bend region wherein the flexular strength of said outer tubular member is reduced compared to other portions of said outer tubular member.

6. The surgical assembly of claim 5 wherein said bend region comprises a plurality of notches extending from the outer surface of said tubular member to the lumen of said tubular member that serve to reduce the overall flexural strength of said bend region relative to that of the remainder of the elongate tubular member.

7. The surgical assembly of claim 6, wherein said plurality of notches comprises (a) a first series of notches disposed on a top side of said bend region and (b) a second series of notches disposed on an opposed bottom side of said bend region.

8. The surgical assembly of claim 7, wherein said second series of notches is offset from and centered between said first series of notches.

9. The surgical assembly of claim 1, wherein said first proximal hub assembly comprises an externally threaded distal portion configured such that when said hub assembly is mounted in a shaver handpiece said threaded distal portion protrudes beyond the distal-most surface of said shaver handpiece.

10. The surgical assembly of claim 9 further comprising a stabilizing element having a central cannulation wherein are formed threads complementary to the threads of said externally threaded distal portion of said first proximal hub assembly, and a proximal-most surface, such that when the stabilizing element is threaded onto said threaded distal portion of said first proximal hub assembly the proximal-most surface of the stabilizing element contacts the distal-most surface of the handpiece in which said surgical assembly is mounted so as to minimize movement of said surgical assembly relative to said handpiece.

* * * * *